(12) United States Patent
Ghasemi et al.

(10) Patent No.: US 12,142,619 B2
(45) Date of Patent: Nov. 12, 2024

(54) PIXEL WITH ENHANCED DRAIN

(71) Applicant: Quantum-Si Incorporated, Guilford, CT (US)

(72) Inventors: Farshid Ghasemi, Guilford, CT (US); Todd Rearick, Cheshire, CT (US)

(73) Assignee: Quantum-Si Incorporated, Branford, CT (US)

( * ) Notice: Subject to any disclaimer, the term of this patent is extended or adjusted under 35 U.S.C. 154(b) by 92 days.

(21) Appl. No.: 17/086,094

(22) Filed: Oct. 30, 2020

(65) Prior Publication Data
US 2021/0134855 A1     May 6, 2021

Related U.S. Application Data

(60) Provisional application No. 62/928,596, filed on Oct. 31, 2019.

(51) Int. Cl.
| | |
|---|---|
| *H01L 27/146* | (2006.01) |
| *C12Q 1/6869* | (2018.01) |
| *G01N 21/64* | (2006.01) |

(52) U.S. Cl.
CPC ........ *H01L 27/1461* (2013.01); *C12Q 1/6869* (2013.01); *G01N 21/6428* (2013.01);
(Continued)

(58) Field of Classification Search
CPC ........... H01L 27/1461; H01L 27/14689; H01L 27/14643; H01L 27/14612;
(Continued)

(56) References Cited

U.S. PATENT DOCUMENTS

| | | |
|---|---|---|
| 4,315,159 A | 2/1982 | Niwa et al. |
| 5,961,924 A | 10/1999 | Reichert et al. |
| (Continued) | | |

FOREIGN PATENT DOCUMENTS

| | | |
|---|---|---|
| CN | 109997229 A | 7/2019 |
| EP | 3 483 938 A1 | 5/2019 |
| (Continued) | | |

OTHER PUBLICATIONS

Invitation to Pay Additional Fees for International Application No. PCT/US2020/039868 dated Oct. 22, 2020.
(Continued)

*Primary Examiner* — Sitaramarao S Yechuri
(74) *Attorney, Agent, or Firm* — Wolf, Greenfield & Sacks, P.C.

(57) ABSTRACT

Some embodiments relate to an integrated circuit, comprising: a pixel, comprising: a photodetection region; and a drain configured to discard charge carriers from within a semiconductor region of the pixel outside of the photodetection region. Some embodiments relate to an integrated circuit, comprising: a pixel, comprising: a photodetection region; and a drain configured to discard charge carriers from the photodetection region, wherein the drain comprises a semiconductor region and the semiconductor region is contacted by a metal contact. Some embodiments relate to an integrated circuit, comprising: a pixel, comprising: a photodetection region; and a drain configured to discard charge carriers from the photodetection region, wherein the drain comprises a semiconductor region that to which electrical contact is made through a conductive path that does not include a polysilicon electrode.

45 Claims, 18 Drawing Sheets
(6 of 18 Drawing Sheet(s) Filed in Color)

(52) U.S. Cl.
CPC .. *H01L 27/14643* (2013.01); *H01L 27/14689* (2013.01); *G01N 2021/6439* (2013.01)

(58) Field of Classification Search
CPC ........ H01L 27/14654; H01L 27/14603; C12Q 1/6869; G01N 21/6428; G01N 2021/6439
See application file for complete search history.

(56) References Cited

U.S. PATENT DOCUMENTS

| | | | |
|---|---|---|---|
| 5,986,297 A | 11/1999 | Guidash et al. | |
| 6,303,919 B1 | 10/2001 | Yokomichi et al. | |
| 6,316,814 B1 | 11/2001 | Nagata et al. | |
| 6,624,456 B2 | 9/2003 | Fossum et al. | |
| 6,787,308 B2 | 9/2004 | Balasubramanian et al. | |
| 6,917,726 B2 | 7/2005 | Levene et al. | |
| 7,175,811 B2 | 2/2007 | Bach et al. | |
| 7,426,322 B2 | 9/2008 | Hyde | |
| 7,738,086 B2 | 6/2010 | Shepard et al. | |
| 7,820,983 B2 | 10/2010 | Lundquist et al. | |
| 7,834,329 B2 | 11/2010 | Lundquist et al. | |
| 7,838,847 B2 | 11/2010 | Lundquist et al. | |
| 8,053,742 B2 | 11/2011 | Lundquist et al. | |
| 8,207,509 B2 | 6/2012 | Lundquist et al. | |
| 8,274,040 B2 | 9/2012 | Zhong et al. | |
| 8,278,728 B2 | 10/2012 | Murshid | |
| 8,465,699 B2 | 6/2013 | Fehr et al. | |
| 8,471,219 B2 | 6/2013 | Lundquist et al. | |
| 8,471,230 B2 | 6/2013 | Zhong et al. | |
| 8,502,169 B2 | 8/2013 | Rigneault et al. | |
| 8,618,507 B1 | 12/2013 | Lundquist et al. | |
| 8,860,862 B2 | 10/2014 | Kobayashi et al. | |
| 8,878,264 B2 | 11/2014 | Velichko et al. | |
| 9,029,802 B2 | 5/2015 | Lundquist et al. | |
| 9,157,864 B2 | 10/2015 | Fehr et al. | |
| 9,222,123 B2 | 12/2015 | Zhong et al. | |
| 9,222,133 B2 | 12/2015 | Lundquist et al. | |
| 9,223,084 B2 | 12/2015 | Grot et al. | |
| 9,372,308 B1 | 6/2016 | Saxena et al. | |
| 9,587,276 B2 | 3/2017 | Lundquist et al. | |
| 9,606,060 B2 | 3/2017 | Chen et al. | |
| 9,658,161 B2 | 5/2017 | Saxena et al. | |
| 9,666,748 B2 | 5/2017 | Leobandung | |
| 9,719,138 B2 | 8/2017 | Zhong et al. | |
| 9,765,395 B2 | 9/2017 | Goldsmith | |
| 9,917,126 B1 | 3/2018 | Lagrasta et al. | |
| 9,921,157 B2 | 3/2018 | Rothberg et al. | |
| 9,946,017 B2 | 4/2018 | Saxena et al. | |
| 10,018,764 B2 | 7/2018 | Grot et al. | |
| 10,090,429 B2 | 10/2018 | Leobandung | |
| 10,138,515 B2 | 11/2018 | Fehr et al. | |
| 10,280,457 B2 | 5/2019 | Zhong et al. | |
| 10,310,178 B2 | 6/2019 | Saxena et al. | |
| 10,487,356 B2 | 11/2019 | Lundquist et al. | |
| 10,566,359 B1 | 2/2020 | Leung | |
| 10,578,788 B2 | 3/2020 | Grot et al. | |
| 10,655,172 B2 | 5/2020 | Rank et al. | |
| 10,724,090 B2 | 7/2020 | McCaffrey et al. | |
| 11,804,499 B2 | 10/2023 | Yang et al. | |
| 2002/0180054 A1* | 12/2002 | Zambrano | H01L 21/76877 257/E21.585 |
| 2002/0182716 A1 | 12/2002 | Weisbuch et al. | |
| 2003/0049905 A1* | 3/2003 | Nitta | H01L 27/105 438/258 |
| 2003/0174992 A1 | 9/2003 | Levene et al. | |
| 2006/0132632 A1 | 6/2006 | Ihara | |
| 2006/0208285 A1 | 9/2006 | Inoue et al. | |
| 2008/0265296 A1 | 10/2008 | Uya | |
| 2009/0166514 A1 | 7/2009 | Tokuda et al. | |
| 2009/0303366 A1 | 12/2009 | Gambino et al. | |
| 2010/0065726 A1 | 3/2010 | Zhong et al. | |
| 2010/0187401 A1 | 7/2010 | Kawahito | |
| 2013/0070131 A1 | 3/2013 | Ohkubo et al. | |
| 2013/0116153 A1 | 5/2013 | Bowen et al. | |
| 2013/0134299 A1* | 5/2013 | Durini Romero | H01L 27/14614 257/222 |
| 2014/0077283 A1 | 3/2014 | Lenchenkov | |
| 2014/0197301 A1 | 7/2014 | Velichko et al. | |
| 2014/0239155 A1 | 8/2014 | Ohkubo | |
| 2014/0291793 A1 | 10/2014 | Tanaka | |
| 2014/0327051 A1 | 11/2014 | Ahn et al. | |
| 2015/0002718 A1 | 1/2015 | Nomura | |
| 2015/0041850 A1* | 2/2015 | Saikaku | H01L 29/7819 257/334 |
| 2015/0060966 A1 | 3/2015 | Lenchenkov et al. | |
| 2015/0264287 A1 | 9/2015 | Shimotsusa et al. | |
| 2015/0325606 A1 | 11/2015 | Togashi et al. | |
| 2015/0340393 A1 | 11/2015 | Tamaki et al. | |
| 2015/0372038 A1 | 12/2015 | Lee et al. | |
| 2016/0013227 A1 | 1/2016 | Kim et al. | |
| 2016/0211306 A1 | 7/2016 | Choi et al. | |
| 2016/0381310 A1 | 12/2016 | Lenchenkov et al. | |
| 2017/0146479 A1 | 5/2017 | Levine et al. | |
| 2017/0170358 A1* | 6/2017 | Dixon | H01L 31/112 |
| 2018/0114806 A1 | 4/2018 | Kim | |
| 2018/0130840 A1 | 5/2018 | Kobayashi et al. | |
| 2018/0180546 A1* | 6/2018 | Rothberg | H01L 27/14687 |
| 2018/0197910 A1 | 7/2018 | Lee et al. | |
| 2018/0226439 A1 | 8/2018 | Oda et al. | |
| 2018/0247969 A1 | 8/2018 | Mori et al. | |
| 2019/0025511 A1 | 1/2019 | Rothberg et al. | |
| 2019/0292590 A1 | 9/2019 | Zhong et al. | |
| 2019/0378864 A1* | 12/2019 | Innocent | H04N 25/75 |
| 2019/0391010 A1 | 12/2019 | Thurston et al. | |
| 2020/0408690 A1 | 12/2020 | Yang et al. | |
| 2023/0253421 A1 | 8/2023 | Yang et al. | |

FOREIGN PATENT DOCUMENTS

| | | |
|---|---|---|
| WO | WO 2011/153962 A1 | 12/2011 |
| WO | WO 2019/026606 A1 | 2/2019 |
| WO | WO 2019/093479 A1 | 5/2019 |

OTHER PUBLICATIONS

International Search Report and Written Opinion for International Application No. PCT/US2020/039868 dated Dec. 15, 2020.
International Search Report and Written Opinion for International Application No. PCT/US2020/058134 dated Feb. 17, 2021.
Hale, Fibre Optic Sensors using Adiabatically Tapered Single Mode Fibres. Dissertation submitted to the University of Cambridge. Feb. 1994. 209 pages.
Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.
Taitt et al., Evanescent wave fluorescence biosensors. Biosens Bioelectron. Jun. 2005;20(12):2470-87. Epub Dec. 8, 2004.
U.S. Appl. No. 16/913,688, filed Jun. 26, 2020, Yang et al.
PCT/US2020/039868, Oct. 22, 2020, Invitation to Pay Additional Fees.
PCT/US2020/039868, Dec. 15, 2020, International Search Report and Written Opinion.
PCT/US2020/058134, Feb. 17, 2021, International Search Report and Written Opinion.
International Preliminary Report on Patentability for International Application No. PCT/US2020/039868 dated Jan. 6, 2022.
International Preliminary Report on Patentability for International Application No. PCT/US2020/058134 dated May 12, 2022.

* cited by examiner

PIXEL WITH ENHANCED DRAIN

RELATED APPLICATIONS

This application claims the benefit under 35 U.S.C. § 119(e) of the filing date of U.S. Provisional Application Ser. No. 62/928,596, filed Oct. 31, 2019, the entire contents of which is incorporated herein by reference.

BACKGROUND

Photodetectors are used to detect light in a variety of applications. Integrated photodetectors have been developed that produce an electrical signal indicative of the intensity of incident light. Integrated photodetectors for imaging applications include an array of pixels to detect the intensity of light received from across a scene. Examples of integrated photodetectors include charge coupled devices (CCDs) and Complementary Metal Oxide Semiconductor (CMOS) image sensors.

SUMMARY

Some embodiments relate to an integrated circuit, comprising: a pixel, comprising: a photodetection region; and a drain configured to discard charge carriers from within a semiconductor region of the pixel outside of the photodetection region.

The drain may be configured such that the drain does not extract charge carriers from the photodetection region when the drain is biased at a voltage in an operational voltage range of the pixel.

The drain may be maintained at a fixed voltage.

The voltage of the drain may be variable.

The drain may comprise a semiconductor region.

The integrated circuit may further comprise a conductive contact that contacts the semiconductor region.

The conductive contact may be a metal plug.

The conductive contact may not extend outside an area of the drain in plan view.

The semiconductor region may be doped.

The semiconductor region may be n-type doped.

The integrated circuit may further comprise a second semiconductor region that is p-type doped under the semiconductor region that is n-type doped.

The semiconductor region may be spaced apart from the photodetection region.

The drain may be a first drain and the pixel may further comprise a second drain.

The first drain may be on a first side of the photodetection region and the second drain may be on a second side of the photodetection region.

The pixel may further comprise a third drain.

The third drain may be within a readout region of the pixel.

The third drain may be configured to discard carriers from the photodetection region.

The drain may comprise a pn junction or a Schottky junction.

The drain may establish a depletion region that overlaps with a depletion region of the photodetection region.

The drain may configured to collect and discard charge carriers under the pixel circuitry or one or more doped regions.

The drain may be a first drain and the integrated circuit may further comprise a second drain, wherein the second drain is configured to discard carriers from the photodetection region.

Some embodiments relate to an integrated circuit, comprising: a pixel, comprising: a photodetection region; and a drain configured to discard charge carriers from the photodetection region, wherein the drain comprises a semiconductor region and the semiconductor region is contacted by a metal contact.

The semiconductor region may be in contact with the photodetection region.

The semiconductor region may be doped.

The semiconductor region may be separated from a photodetection region by a second semiconductor region of opposite doping type from that of the semiconductor region.

The drain may be controlled to be at a first voltage when the drain pulls charge carriers out of the photodetection region and is controlled to be at a second voltage when the drain does not pull charge carriers out of the photodetection region.

The drain may be configured to produce a potential barrier between the photodetection region and the drain when the drain does not discard charge carriers from the photodetection region.

The metal contact may not extend outside an area of the drain in plan view.

The integrated circuit may further comprise a silicide material between the metal contact and the drain.

There may be no polysilicon in an electrical path between the metal contact and the drain.

Some embodiments relate to an integrated circuit, comprising: a pixel, comprising: a photodetection region; and a drain configured to discard charge carriers from the photodetection region, wherein the drain comprises a semiconductor region that to which electrical contact is made through a conductive path that does not include a polysilicon electrode.

The semiconductor region may be in contact with the photodetection region.

The semiconductor region may be doped.

The semiconductor region may be separated from a photodetection region by a second semiconductor region of opposite doping type from that of the semiconductor region.

The drain may be controlled to be at a first voltage when the drain pulls charge carriers out of the photodetection region and controlled to be at a second voltage when the drain does not pull charge carriers out of the photodetection region.

The drain may be configured to produce a potential barrier between the photodetection region and the drain when the drain does not discard charge carriers from the photodetection region.

The metal contact may not extend outside an area of the drain in plan view.

Some embodiments relate to an integrated circuit, comprising: a pixel, comprising: a photodetection region; and a photodiode configured to collect and drain unwanted charge carriers.

The photodiode may be a first photodiode and the photodetection region may comprise a second photodiode.

The first and second photodiodes may have a same doping profile.

The first and second photodiodes may be pinned photodiodes.

The photodetection region may comprise a gate to transfer charge carriers from the photodetection region to a charge storage region.

The photodetection region may be a first photodetection region and the photodiode may be between the first photodetection region and a second photodetection region.

The photodiode may be configured to collect and drain unwanted charge carriers from between the first and second photodetection regions.

Some embodiments relate to a method of manufacturing an integrated circuit, the method comprising: forming a pixel comprising a photodetection region and a drain configured to discard charge carriers from within a semiconductor region of the pixel outside of the photodetection region.

Some embodiments relate to a method of manufacturing an integrated circuit, the method comprising: forming a pixel comprising a photodetection region and a drain configured to discard charge carriers from the photodetection region; and forming a metal contact contacting the drain.

Some embodiments relate to a method of manufacturing an integrated circuit, the method comprising: forming a pixel comprising a photodetection region and a drain configured to discard charge carriers from the photodetection region; and electrically contacting the drain through a conductive path that does not include a polysilicon electrode.

Some embodiments relate to a method of manufacturing an integrated circuit, the method comprising: forming a pixel comprising a photodetection region and a photodiode configured to collect and drain unwanted charge carriers.

The foregoing summary is provided by way of illustration and is not intended to be limiting.

BRIEF DESCRIPTION OF THE DRAWINGS

The present patent or patent application file contains at least one drawing executed in color. Copies of this patent or patent application publication with color drawings will be provided by the Office upon request and payment of the necessary fee.

DETAILED DESCRIPTION

Figure 1:
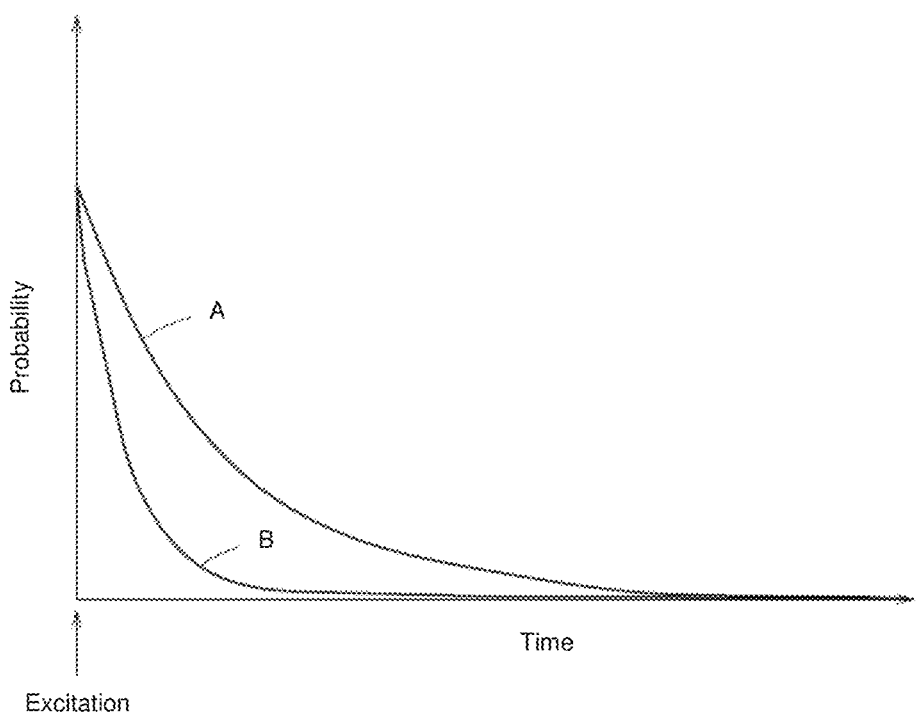
FIG. 1 plots the probability of a photon being emitted as a function of time for two markers with different lifetimes.

Described herein is an integrated photodetector that can accurately measure, or "time-bin," the timing of arrival of incident photons. In some embodiments, the integrated photodetector can measure the arrival of photons with nanosecond or picosecond resolution. Such a photodetector may find application in a variety of applications including molecular detection/quantitation, which may be applied to sequencing of nucleic acids (e.g., DNA sequencing). Such a photodetector can facilitate time-domain analysis of the arrival of incident photons from luminescent molecules used to label nucleotides, thereby enabling identification and sequencing of nucleotides based upon luminance lifetimes. Other examples of applications of the integrated photodetector include fluorescence lifetime imaging and time-of-flight imaging, as discussed further below.

Discussion of Time Domain Measurements for Molecular Detection/Quantitation

Detection and quantitation of biological samples may be performed using biological assays ("bioassays"). Bioassays conventionally involve large, expensive laboratory equipment requiring research scientists trained to operate the equipment and perform the bioassays. Bioassays are conventionally performed in bulk such that a large amount of a particular type of sample is necessary for detection and quantitation. Some bioassays are performed by tagging samples with luminescent markers that emit light of a particular wavelength. The samples are illuminated with a light source to cause luminescence, and the luminescent light is detected with a photodetector to quantify the amount of light emitted by the markers. Bioassays using luminescent tags and/or reporters conventionally involve expensive laser light sources to illuminate samples and complicated luminescent detection optics and electronics to collect the light from the illuminated samples.

In some embodiments, an integrated photodetector as described herein can detect the luminance characteristics of biological and/or chemical sample(s) in response to excitation. More specifically, such an integrated photodetector can detect the temporal characteristics of light received from the sample(s). Such an integrated photodetector can enable detecting and/or discriminating the luminance lifetime, e.g., the fluorescence lifetime, of light emitted by a luminescent molecule in response to excitation. In some embodiments, identification and/or quantitative measurements of sample(s) can be performed based on detecting and/or discriminating luminance lifetimes. For example, in some embodiments sequencing of a nucleic acid (e.g., DNA, RNA) may be performed by detecting and/or discriminating luminance lifetimes of luminescent molecules attached to respective nucleotides. Each luminescent molecule may be directly attached (e.g., bonded) to a corresponding nucleotide or indirectly attached to a corresponding nucleotide via a linker molecule that is bonded to the nucleotide and the luminescent molecule.

In some embodiments, an integrated photodetector having a number of photodetection structures and associated electronics, termed "pixels," can enable measurement and analysis of a plurality of samples in parallel (e.g., hundreds, thousands, millions or more), which can reduce the cost of performing complex measurements and rapidly advance the rate of discoveries. In some embodiments, each pixel of the photodetector may detect light from a sample, which may be a single molecule or more than one molecule. In some embodiments, such an integrated photodetector can be used for dynamic real time applications such as nucleic acid (e.g., DNA, RNA) sequencing.

Detection/Quantitation of Molecules Using Luminance Lifetimes

An integrated circuit having an integrated photodetector according to aspects of the present application may be designed with suitable functions for a variety of detection and imaging applications. As described in further detail below, such an integrated photodetector can have the ability to detect light within a detection time period, also termed a "detection period" or "time bin." To collect information regarding the time of arrival of the light, charge carriers are generated in response to incident photons and can be directed into a time bin based on their time of arrival.

An integrated photodetector according to some aspects of the present application may be used for differentiating among light emission sources, including luminescent molecules, such as fluorophores. Luminescent molecules vary in the wavelength of light they emit, the temporal characteristics of the light they emit (e.g., their emission decay time periods), and their response to excitation energy. Accordingly, luminescent molecules may be identified or discriminated from other luminescent molecules based on detecting these properties. Such identification or discrimination techniques may be used alone or in any suitable combination.

In some embodiments, an integrated photodetector as described in the present application can measure or discriminate luminance lifetimes, such as fluorescence lifetimes. Fluorescence lifetime measurements are based on exciting one or more fluorescent molecules, and measuring the time variation in the emitted luminescence. The probability of a fluorescent molecule to emit a photon after the fluorescent molecule reaches an excited state decreases exponentially over time. The rate at which the probability decreases may be characteristic of a fluorescent molecule, and may be different for different fluorescent molecules. Detecting the temporal characteristics of light emitted by fluorescent molecules may allow identifying fluorescent molecules and/or discriminating fluorescent molecules with respect to one another. Luminescent molecules are also referred to herein as luminescent markers, or simply "markers".

After reaching an excited state, a marker may emit a photon with a certain probability at a given time. The probability of a photon being emitted from an excited marker may decrease over time after excitation of the marker. The decrease in the probability of a photon being emitted over time may be represented by an exponential decay function $p(t)=e^{-t/\tau}$, where p(t) is the probability of photon emission at a time, t, and $\tau$ is a temporal parameter of the marker. The temporal parameter $\tau$ indicates a time after excitation when the probability of the marker emitting a photon is a certain value. The temporal parameter, $\tau$, is a property of a marker that may be distinct from its absorption and emission spectral properties. Such a temporal parameter, $\tau$, is referred to as the luminance lifetime, the fluorescence lifetime or simply the "lifetime" of a marker.

FIG. 1 plots the probability of a photon being emitted as a function of time for two markers with different lifetimes. The marker represented by probability curve B has a probability of emission that decays more quickly than the probability of emission for the marker represented by probability curve A. The marker represented by probability curve B has a shorter temporal parameter, $\tau$, or lifetime than the marker represented by probability curve A. Markers may have fluorescence lifetimes ranging from 0.1-20 ns, in some embodiments. However, the techniques described herein are not limited as to the lifetimes of the marker(s) used.

The lifetime of a marker may be used to distinguish among more than one marker, and/or may be used to identify marker(s). In some embodiments, fluorescence lifetime measurements may be performed in which a plurality of markers having different lifetimes are excited by an excitation source. As an example, four markers having lifetimes of 0.5, 1, 2, and 3 nanoseconds, respectively, may be excited by a light source that emits light having a selected wavelength (e.g., 635 nm, by way of example). The markers may be identified or differentiated from each other based on measuring the lifetime of the light emitted by the markers. However, the lifetime itself need not be calculated, as other temporal characteristics of the light emitted by markers may be used to distinguish between them.

Fluorescence lifetime measurements may use relative intensity measurements by comparing how intensity changes over time, as opposed to absolute intensity values. As a result, fluorescence lifetime measurements may avoid some of the difficulties of absolute intensity measurements. Absolute intensity measurements may depend on the concentration of fluorophores present and calibration steps may be needed for varying fluorophore concentrations. By contrast, fluorescence lifetime measurements may be insensitive to the concentration of fluorophores.

Luminescent markers may be exogenous or endogenous. Exogenous markers may be external luminescent markers used as a reporter and/or tag for luminescent labeling. Examples of exogenous markers may include fluorescent molecules, fluorophores, fluorescent dyes, fluorescent stains, organic dyes, fluorescent proteins, enzymes, and/or quantum dots. Such exogenous markers may be conjugated to a probe or functional group (e.g., molecule, ion, and/or ligand) that specifically binds to a particular target or component. Attaching an exogenous tag or reporter to a probe allows identification of the target through detection of the presence of the exogenous tag or reporter. Examples of probes may include proteins, nucleic acids such as DNA molecules or RNA molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

While exogenous markers may be added to a sample or region, endogenous markers may be already part of the sample or region. Endogenous markers may include any luminescent marker present that may luminesce or "autofluoresce" in the presence of excitation energy. Autofluorescence of endogenous fluorophores may provide for label-free and noninvasive labeling without requiring the introduction of endogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or prophyrins, by way of example and not limitation.

Differentiating between markers by lifetime measurements may allow for fewer wavelengths of excitation light to be used than when the markers are differentiated by measurements of emission spectra. In some embodiments, sensors, filters, and/or diffractive optics may be reduced in number or eliminated when using fewer wavelengths of excitation light and/or luminescent light. In some embodiments, labeling may be performed with markers that have different lifetimes, and the markers may be excited by light having the same excitation wavelength or spectrum. In some embodiments, an excitation light source may be used that emits light of a single wavelength or spectrum, which may reduce the cost. However, the techniques described herein are not limited in this respect, as any number of excitation light wavelengths or spectra may be used. In some embodiments, an integrated photodetector may be used to determine both spectral and temporal information regarding received light. In some embodiments a quantitative analysis of the types of molecule(s) present may be performed by determining a temporal parameter, an intensity parameter, a spectral parameter, or a combination of parameters of the emitted luminescence from a marker.

An integrated photodetector that detects the arrival time of incident photons may reduce additional optical filtering (e.g., optical spectral filtering) requirements. As described below, an integrated photodetector according to the present application may include a drain to remove photogenerated carriers at particular times. By removing photogenerated carriers in this manner, unwanted charge carriers produced in response to an excitation light pulse may be discarded without the need for optical filtering to prevent reception of light from the excitation pulse. Such a photodetector may reduce overall design integration complexity, optical and/or filtering components, and/or cost.

In some embodiments, a fluorescence lifetime may be determined by measuring the time profile of the emitted luminescence by aggregating collected charge carriers in one or more time bins of the integrated photodetector to detect luminance intensity values as a function of time. In some embodiments, the lifetime of a marker may be determined by performing multiple measurements where the marker is excited into an excited state and then the time when a photon emits is measured. For each measurement, the excitation source may generate a pulse of excitation light directed to the marker, and the time between the excitation pulse and subsequent photon event from the marker may be determined. Additionally or alternatively, when an excitation pulse occurs repeatedly and periodically, the time between when a photon emission event occurs and the subsequent excitation pulse may be measured, and the measured time may be subtracted from the time interval between excitation pulses (i.e., the period of the excitation pulse waveform) to determine the time of the photon absorption event.

By repeating such experiments with a plurality of excitation pulses, the number of instances a photon is emitted from the marker within a certain time interval after excitation may be determined, which is indicative of the probability of a photon being emitted within such a time interval after excitation. The number of photon emission events collected may be based on the number of excitation pulses emitted to the marker. The number of photon emission events over a measurement period may range from 50-10,000,000 or more, in some embodiments, however, the techniques described herein are not limited in this respect. The number of instances a photon is emitted from the marker within a certain time interval after excitation may populate a histogram representing the number of photon emission events that occur within a series of discrete time intervals. A curve fitting algorithm may be used to fit a curve to the recorded histogram, resulting in a function representing the probability of a photon to be emitted after excitation of the marker at a given time. An exponential decay function, such as $p(t)=e^{-t/\tau}$, may be used to approximately fit the histogram data. From such a curve fitting, the temporal parameter or lifetime may be determined. The determined lifetime may be compared to known lifetimes of markers to identify the type of marker present. However, as mentioned above, the lifetime of a marker need not be calculated, as other temporal characteristics may be used to distinguish between markers, such as temporal characteristics that are measured directly or otherwise derived from measurements.

In some instances, the probability of a photon emission event and thus the lifetime or other temporal characteristics of a marker may change based on the surroundings and/or conditions of the marker. For example, the lifetime of a marker confined in a volume with a diameter less than the wavelength of the excitation light may be smaller than when the marker is not in the volume. Lifetime measurements with known markers under conditions similar to when the markers are used for labeling may be performed. The lifetimes determined from such measurements with known markers may be used when identifying a marker.

Sequencing Using Luminance Lifetime Measurements

Individual pixels of an integrated photodetector may be capable of fluorescence lifetime measurements used to identify fluorescent tags and/or reporters that label one or more targets, such as molecules or specific locations on molecules. Any one or more molecules of interest may be labeled with a fluorophore, including proteins, amino acids, enzymes, lipids, nucleotides, DNA, and RNA. When combined with detecting spectra of the emitted light or other labeling techniques, fluorescence lifetime may increase the total number of fluorescent tags and/or reporters that can be used. Identification based on lifetime may be used for single molecule analytical methods to provide information about characteristics of molecular interactions in complex mixtures where such information would be lost in ensemble averaging and may include protein-protein interactions, enzymatic activity, molecular dynamics, and/or diffusion on membranes. Additionally, fluorophores with different fluorescence lifetimes may be used to tag target components in various assay methods that are based on presence of a labeled component. In some embodiments, components may be separated, such as by using microfluidic systems, based on detecting particular lifetimes of fluorophores.

Measuring fluorescence lifetimes may be used in combination with other analytical methods. For an example, fluorescence lifetimes may be used in combination with fluorescence resonance energy transfer (FRET) techniques to discriminate between the states and/or environments of donor and acceptor fluorophores located on one or more molecules. Such measurements may be used to determine the distance between the donor and the acceptor. In some instances, energy transfer from the donor to the acceptor may decrease the lifetime of the donor. In another example, fluorescence lifetime measurements may be used in combination with DNA sequencing techniques where four fluorophores having different lifetimes may be used to label the four different nucleotides (A, T, G, C) in a DNA molecule with an unknown sequence of nucleotides. The fluorescence lifetimes, instead of emission spectra, of the fluorophores may be used to identify the sequence of nucleotides. By using fluorescence lifetime or another temporal characteristic instead of emission spectra for certain techniques, accuracy and measurement resolution may increase because artifacts due to absolute intensity measurements are reduced. Additionally, lifetime measurements may reduce the complexity and/or expense of the system because fewer excitation energy wavelengths are required and/or fewer emission energy wavelengths need be detected.

The methods described herein may be used for sequencing of nucleic acids, such as DNA sequencing or RNA sequencing. DNA sequencing allows for the determination of the order and position of nucleotides in a target nucleic acid molecule. Technologies used for DNA sequencing vary greatly in the methods used to determine the nucleic acid sequence as well as in the rate, read length, and incidence of errors in the sequencing process. A number of DNA sequencing methods are based on sequencing by synthesis, in which the identity of a nucleotide is determined as the nucleotide is incorporated into a newly synthesized strand of nucleic acid that is complementary to the target nucleic acid. Many sequencing by synthesis methods require the presence of a population of target nucleic acid molecules (e.g., copies of a target nucleic acid) or a step of amplification of the target nucleic acid to achieve a population of target nucleic acids. Improved methods for determining the sequence of single nucleic acid molecules is desired.

There have been recent advances in sequencing single nucleic acid molecules with high accuracy and long read length. The target nucleic acid used in single molecule sequencing technology, for example the SMRT technology developed by Pacific Biosciences, is a single stranded DNA template that is added to a sample well containing at least one component of the sequencing reaction (e.g., the DNA polymerase) immobilized or attached to a solid support such as the bottom of the sample well. The sample well also contains deoxyribonucleoside triphosphates, also referred to a "dNTPs," including adenine, cytosine, guanine, and thymine dNTPs, that are conjugated to detection labels, such as fluorophores. Preferably each class of dNTPs (e.g. adenine dNTPs, cytosine dNTPs, guanine dNTPs, and thymine dNTPs) are each conjugated to a distinct detection label such that detection of the signal indicates the identity of the dNTP that was incorporated into the newly synthesized nucleic acid. The detection label may be conjugated to the dNTP at any position such that the presence of the detection label does not inhibit the incorporation of the dNTP into the newly synthesized nucleic acid strand or the activity of the polymerase. In some embodiments, the detection label is conjugated to the terminal phosphate (the gamma phosphate) of the dNTP.

Any polymerase may be used for single molecule DNA sequencing that is capable of synthesizing a nucleic acid complementary to a target nucleic acid. Examples of polymerases include E. coli DNA polymerase I, T7 DNA polymerase, bacteriophage T4 DNA polymerase φ29 (psi29) DNA polymerase, and variants thereof. In some embodiments, the polymerase is a single subunit polymerase. Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In examples in which the detection label conjugated to the dNTP is a fluorophore, its presence is signaled by excitation and a pulse of emission is detected during the step of incorporation. For detection labels that are conjugated to the terminal (gamma) phosphate of the dNTP, incorporation of the dNTP into the newly synthesized strand results in release the beta and gamma phosphates and the detection label, which is free to diffuse in the sample well, resulting in a decrease in emission detected from the fluorophore.

The techniques described herein are not limited as to the detection or quantitation of molecules or other samples, or to performing sequencing. In some embodiments, an integrated photodetector may perform imaging to obtain spatial information regarding a region, object or scene and temporal information regarding the arrival of incident photons using the region, object or scene. In some embodiments, the integrated photodetector may perform luminescence lifetime imaging of a region, object or sample, such as fluorescence lifetime imaging.

Integrated Photodetector for Time Binning Photogenerated Charge Carriers

Some embodiments relate to an integrated circuit having a photodetector that produces charge carriers in response to incident photons and which is capable of discriminating the timing at which the charge carriers are generated. In some embodiments, the integrated circuit may have a single bin (also termed "bin," "charge storage bin" or "charge carrier storage region") for time-binning charge carriers produced in the photodetection region. Charge carriers generated during a detection period are transferred to the bin. Charge carriers generated outside of the detection period are not transferred to the bin. As mentioned above, measurements may be repeated a number of times, and the bin may aggregate charge carriers received within the detection period over a plurality of measurements. The amount of charge stored is then read out. Following read out, the timing of the detection period may be changed, and after re-setting the bin another set of measurements may be performed with a different detection period timing. Charge carriers are then aggregated over another plurality of measurements and the stored charge is again read out. The amount of charge collected in different detection periods can provide information about the timing and/or the intensity of light received by the photodetector. Timing information regarding the time of arrival of photons with respect to a reference time can be obtained from a single bin by altering its detection period timing. Such an integrated circuit can be used in any of a variety of applications, such as those described herein. Examples of an integrated circuit having a direct binning pixel with a single bin are described. In some embodiments, the integrated circuit may include an array of such pixels.

As used herein, the term "semiconductor region" refers to a volume of semiconductor material of any shape that is a portion of a larger semiconductor structure (e.g., a pixel region or chip). A semiconductor region may be doped or undoped unless explicitly recited as doped or undoped. Examples of semiconductor regions include doped and undoped regions, such as implants, diffusions and regions of intrinsic semiconductor material. The term "region of semiconductor" has the same meaning as "semiconductor region".

Direct Binning Pixel

Figure 2:
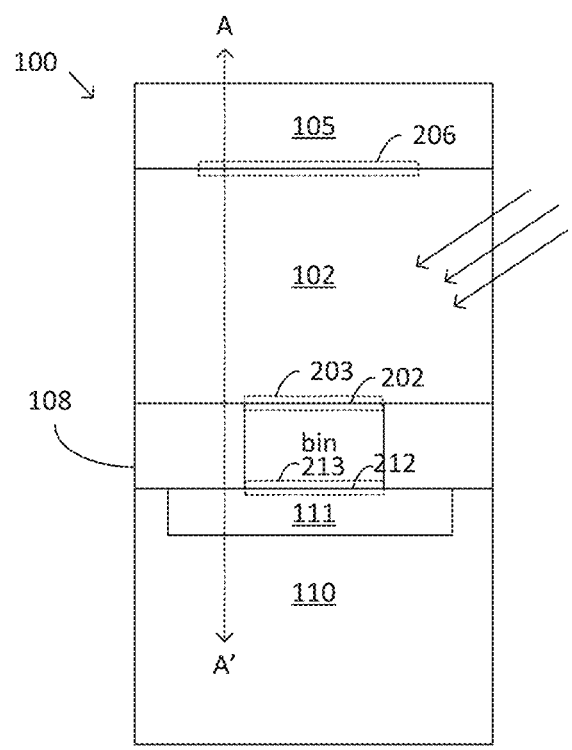
FIG. 2 shows an example of a direct binning pixel.

FIG. 2 shows an example of a pixel 100 in which charge carriers generated in the photon absorption/carrier generation region 102 (also termed a "photodetection region") may be directly transferred to a charge storage bin in charge carrier storage region 108, without an intermediate charge carrier capture region between them. Such a pixel is termed a "direct binning pixel". The bin may be a single bin, with no other bins being configured to receive charge carriers directly from the photon absorption/carrier generation region 102. FIG. 2 shows an example of a pixel 100 having a single bin in charge carrier storage region 108. Advantages of a single bin pixel over a multi-bin pixel may include improved rejection of excitation light, simplification of design by the reduction of complexity, and lower power consumption due to the need to drive fewer electrodes. The bin may aggregate charge carriers received in a detection period following a reference time or trigger event. Also, as discussed further below, one or more additional storage regions may be present to receive the charge stored in the bin for purposes of readout. For example, transferring the charge stored in the bin to another charge storage region for readout may allow for simultaneous use of the bin for receiving charge carriers and another charge storage region for holding the charge while it is read out.

The pixel 100 may include a semiconductor region, which may be formed of any suitable semiconductor, such as silicon, for example. FIG. 2 shows a plan view with the semiconductor region underneath, and electrodes 206, 203 and 213 formed over the top of the semiconductor region. A charge carrier segregation structure including electrodes 206 and 203 selectively directs photogenerated charge carriers to the bin or to a rejection region 105 at different times. In some embodiments, the photon absorption/carrier generation region 102 may include a photodiode, such as a pinned photodiode, formed in the semiconductor region. The photodiode may be fully depleted. In some embodiments, the photodiode may remain essentially depleted of electrons at all times. In some embodiments, the photodiode is configured to collect single photons. In such embodiments, a single photoelectron may be generated and confined in the photodiode. If formed by a CMOS process, the photodiode may be fully depleted by potentials available within devices produced by a CMOS process. In some embodiments, electrode 203 may be coupled to the diode at least partially surrounding the perimeter of the diode. The electrode 203 may allow rapid charge transfer of confined carriers. Prior to discussing transfer of charge carriers to the bin, the rejection of unwanted carriers by transfer of the unwanted carriers into a rejection region 105 will be described.

Referring again to FIG. 2, direct binning pixel 100 may include a rejection region 105 to drain or otherwise discard charge carriers produced in photon absorption/carrier generation region 102 during a rejection period. A rejection period may be timed to occur during a trigger event, such as an excitation light pulse. Since an excitation light pulse may produce a number of unwanted charge carriers in photon absorption/carrier generation region 102, a potential gradient may be established in pixel 100 to drain such charge carriers to rejection region 105 during a rejection period. As an example, rejection region 105 may include a high potential diffusion area where electrons are drained to a supply voltage. Rejection region 105 may include an electrode 206 that charge couples region 102 directly to rejection region 105. In some embodiments, the electrode 206 may overlie the semiconductor region. The voltage of the electrode 206 may be varied to establish a desired potential gradient in photon absorption/carrier generation region 102. During a rejection period, the voltage of the electrode 206 may be set to a level that draws carriers from the photon absorption/carrier generation region 102 into the electrode 206, and out to the supply voltage. For example, the voltage of the electrode 206 may be set to a positive voltage to attract electrons, such that they are drawn away from the photon absorption/carrier generation region 102 to rejection region 105. During a rejection period, electrode 203 may be set to a potential that forms a potential barrier 202 to prevent the unwanted charge carriers from reaching the bin. Rejection region 105 may be considered a "lateral rejection region" because it allows transferring carriers laterally from region 102 to a drain. In some embodiments, the rejection is in the opposite direction (upwards in FIG. 2) from the photodetection region 102 with respect to the direction of transfer (downwards in FIG. 2) of charge carriers from the photodetection region 102 to the bin. The relative positions of the rejection region 105 and collection region 108 are not limited to opposite sides of the photodiode 102; however.

Following the rejection period, a photogenerated charge carrier produced in photon absorption/carrier generation region 102 may be transferred to the bin. During a detection period, a potential barrier 202 formed by electrode 203 may be lowered, a potential barrier formed by electrode 206 may be raised, and the electrical potential within the semiconductor region between photon absorption/carrier generation region 102 and charge carrier storage region 108 may be establish a potential gradient that causes the photogenerated charge carrier(s) to be directed to the bin. At the end of the detection period the potential barrier 202 is raised to prevent further charge carriers from being transferred into the bin. Accordingly, the bin stores the charge carriers received in the bin during the detection period. The stored charge may then be read out, as discussed further below.

In some embodiments, only a single electrode 203 may be disposed at the boundary between region 102 and the bin to control the potential barrier 202 that allows or prevents transfer of a charge carrier to the bin. However, in some embodiments, the potential barrier 202 may be produced by more than one electrode. The electrode(s) 203 may control a potential barrier 202 to either allow or prevent a charge carrier from entering the bin. The potential barrier 202 may be a single potential barrier between region 102 and the bin.

Figure 3:
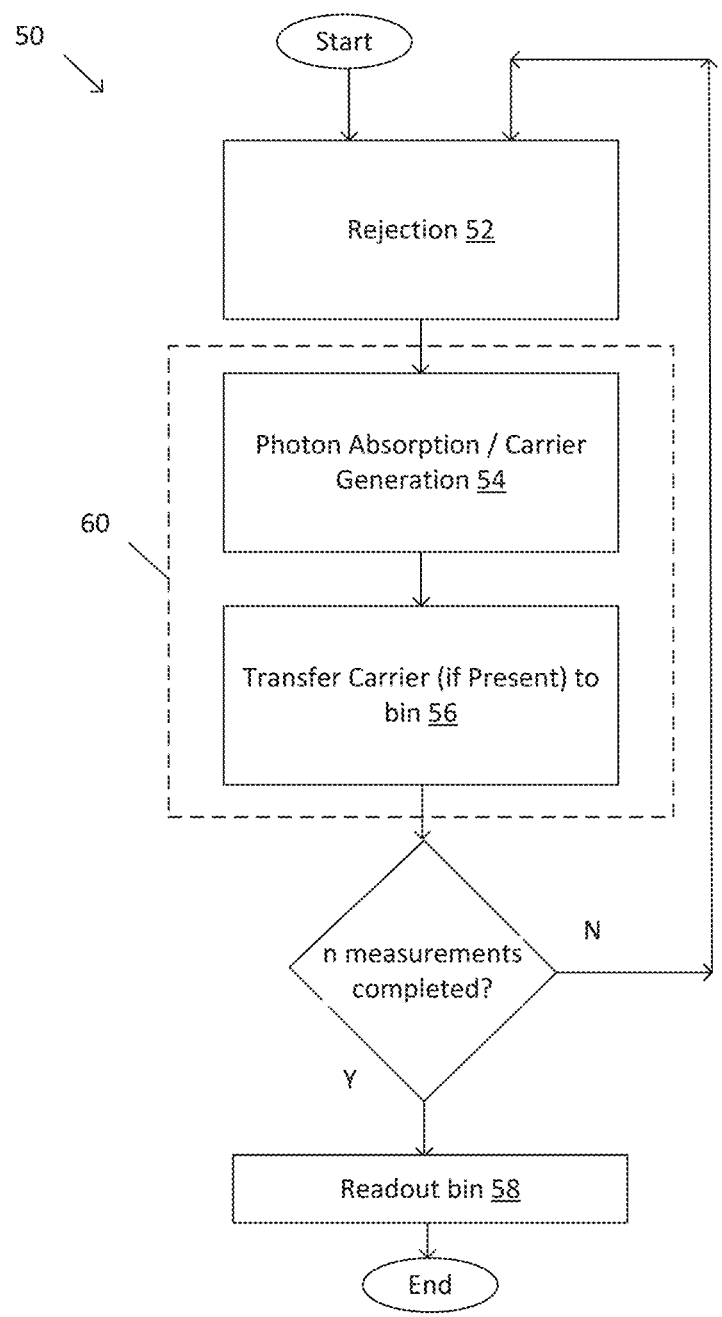
FIG. 3 shows a flowchart of a method of operating a direct binning pixel.

FIG. 3 shows a flowchart of a method 50 of operating pixel 100 that includes performing a plurality of alternating carrier rejection steps 52 and detection steps 60, followed by a readout step 58.

Figure 4A:
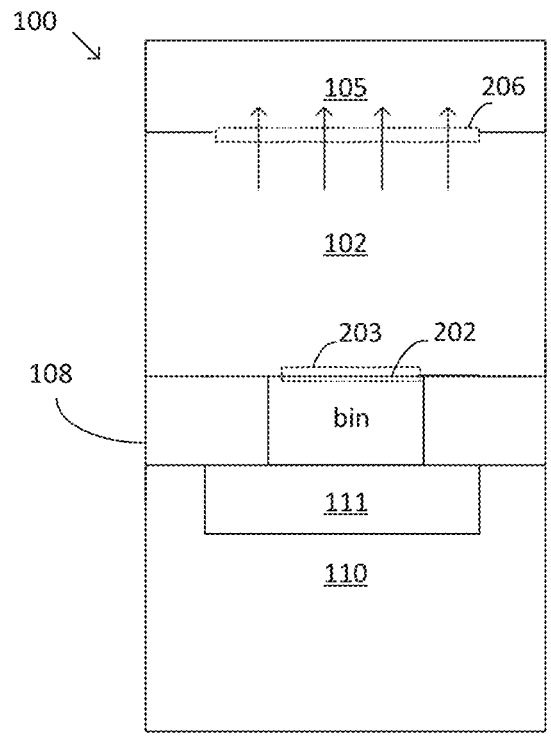
FIG. 4A-C show the direct binning pixel at various stages of the method of FIG. 3.

The operation of pixel 100 during rejection step 52 is illustrated in FIG. 4A. The rejection step 52 occurs for a rejection period. In rejection step 52, the pixel 100 is operated to reject charge carriers produced in region 102 by transferring them to rejection region 105. For example, rejection step 52 may include controlling electrode 206 to produce a potential gradient that drives charge carriers produced in region 102 to rejection region 105. Carriers are rejected by directing them in the upward direction of FIG. 4A. The potential barrier 202 to the bin is raised to prevent unwanted charge from entering the bin.

Rejection step 52 may be timed to occur during a trigger event. A trigger event may be an event that serves as a time reference for time binning arrival of a photon. The trigger event may be an optical pulse or an electrical pulse, for example, and could be a singular event or a repeating, periodic event. In the context of luminance lifetime detection, the trigger event may be the generation or reception of an excitation light pulse to excite a luminescent molecule, such as a fluorophore. In the context of time-of-flight imaging, the trigger event may be a pulse of light (e.g., from a flash) emitted by an imaging device comprising the integrated photodetector. The trigger event can be any event used as a reference for timing the arrival of photons or carriers.

The generation of an excitation light pulse may produce a significant number of photons, some of which may reach the pixel 100 and may produce charge carriers in the photon absorption/carrier generation area 102. Since photogenerated carriers from the excitation light pulse are not desired to be measured, they may be rejected by directing them to a drain in rejection step 52. This can reduce the amount of unwanted signal that otherwise may need to be prevented from arriving by complex optical components, such as a shutter or filter, which may add additional design complexity and/or cost.

Figure 4B:
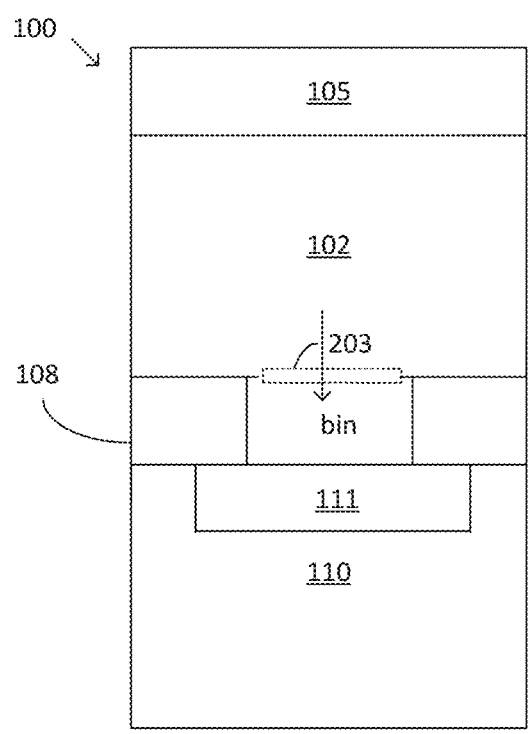

Returning to discussion of FIG. 3, a detection step 60 follows the rejection step 52. As illustrated in FIG. 4B, detection step 60 may include raising a potential barrier to the rejection region 105 (e.g., by modifying the voltage of electrode 206) to prevent photogenerated charge carriers from being discarded. The raising of the potential barrier to the rejection region 105 is the beginning of detection step 60, which has a duration termed a detection period. At the same time or subsequent to the raising of the potential barrier to the rejection region 105, the detection step 60 includes the lowering of potential barrier 202 (e.g., by modifying the voltage of electrode 203) between the region 102 and the bin for a period of time in which charge carriers are allowed to pass from region 102 to the bin. If the potential barrier 202 is lowered subsequent to the raising of the potential barrier to the rejection region 105 any charge carriers photogenerated in the photodetection region 102 remain in the photodetection region 102 until the potential barrier 202 is lowered, and then these charge carriers pass into the bin. Accordingly, the detection period includes both the period of time the potential barrier 202 is lowered as well any period following the raising of the potential barrier to the rejection region 105 before the potential barrier 202 is lowered. A photon may or may not arrive in photodetection region 102 during detection step 60. If a photon arrives in photodetection region 102 and a photogenerated charge carrier is produced (step 54) during the detection period, a potential gradient causes the charge carrier to be directed into the bin (step 56), as illustrated in FIG. 4B. Such a potential gradient may be established in any suitable way, such as using a graded doping concentration and/or one or more electrodes at selected potentials. Then, the potential barrier 202 is raised at the end of the detection period to prevent further charge carriers from being transferred to the bin, which marks the end of the detection period. If a photogenerated charge carrier is produced in region 102 while the potential barrier 202 to the bin is raised, a charge carrier may be confined in region 102 until rejection step 52 occurs again and the charge carrier is discarded. Accordingly, the bin collects the photogenerated charge carriers produced in region 102 during a detection period.

As discussed above, in some applications the probability of receiving a photon and generating a carrier in response to a trigger event may be low (e.g., about 1 in 10,000). Accordingly, a photon may be received in detection step 60 rather infrequently. However, in some embodiments, the quantity of photons received and/or probability of receiving a photon may be higher, as the techniques described herein are not limited to a low quantity of received photons.

Following step 56 the rejection step 52 and detection step 60 may be repeated n−1 times to obtain information (e.g., statistical information) regarding the time periods at which photons tend to arrive after a trigger event. Time-binned charge carriers may be aggregated in the bin as the detection step 60 is repeated. Repeating the detection step 60 may enable aggregating a sufficient number of charge carriers in the bin to provide statistically meaningful results. For example, in the context of fluorescence lifetime measurement, it may be expected that a photon absorption event in response to a photon received from a fluorophore may occur relatively rarely. For example, such an event may be expected to occur once in about 10,000 measurements. Accordingly, a large number of measurements (detection step 60) may need to be performed to aggregate a sufficient number of charge carriers in the bin such that the results are statistically meaningful and/or have a sufficient signal to noise ratio. In some embodiments, the number of measurements n of a fluorophore that may be performed for fluorescence lifetime measurement may be 50,000 or more, 100,000 or more, 200,000 or more, 300,000 or more, 400,000 or more 500,000 or more, one million or more, two million or more five million or more, to enable capturing and binning a sufficient number of charge carriers in each bin (i.e., tens or hundreds, or more, in some embodiments). The measurements may be repeated at a frequency in the MHz range, such as between 50 MHz and 100 MHz, between 25 MHz and 200 MHz, between 10 MHz and 500 MHz, or between 1 MHz and 500 MHz, all ranges being inclusive of endpoints, or at another frequency. In some embodiments, after the measurement is repeated n−1 times, about one hundred carriers (e.g., electrons) may be accumulated in the bin. However, this depends on the number of photons received. In some embodiments, the number of carriers accumulated in the bin may be between 10 and 10,000, such as between 50 and 1,000, or any other suitable number. Method 50 may be performed over any suitable time period in which photons are desired to be captured. The period over which method 50 is performed is termed a "frame". In the context of fluorescence lifetime measurement, a suitable length of a frame may be 10 milliseconds, for example. In some embodiments, a detection step 60 may be repeated at a frequency that is the MHz range. In some embodiments, the bin may have a resolution on the scale of picoseconds or nanoseconds.

Figure 4C:
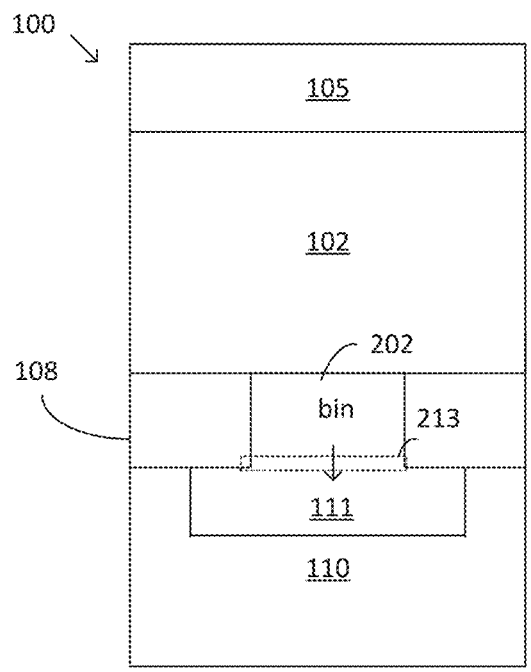

Once the allotted number n of measurements (step 60) has been performed, the method proceeds to step 58 of reading out the bin. In step 58, charge may be transferred from the bin to a readout node 111, which is another charge carrier storage region. The readout node 111 may include a floating diffusion. Alternatively, the bin may itself be a floating diffusion which is used for both charge storage and readout. In this case, 212/213 are absent and 111 is the bin. Transfer of charge from the bin to readout node 111 is illustrated in FIG. 4C. To transfer the charge from each bin, the voltage of electrode 213 may be changed to lower a potential barrier 212 between the bin and the readout node 111. A potential gradient may be established that causes the charge to flow from bin 0 to readout node 111. The charge transferred to readout node 111 may then be converted into a voltage and read out using readout circuitry 110, an example of which is shown in FIG. 5.

In some embodiments, the integrated device may be programmable to enable changing the timing of the bin. The electrodes may be controlled by a control circuit that sets a suitable timing and adjusts the timing between frames. In some embodiments, the timing for the time bin may be set based upon the timing of a trigger event that initiates a measurement period for a measurement 60. In the fluorescence lifetime measurement context, the timing for the time bin may be set in response to detecting the timing of an excitation pulse that excites a fluorophore. For example, when an excitation light pulse reaches the pixel 100, a surge of carriers may travel from the photon absorption/carrier generation region 102 to the drain. The accumulation of photogenerated carriers at the drain in response to the excitation pulse may cause a change in voltage of the drain. Accordingly, in some embodiments the excitation pulse may be detected by detecting the voltage of the drain. For example, a comparator may compare the voltage of the drain to a threshold, and may produce a pulse when the voltage of the drain exceeds the threshold. The timing of the pulse may be indicate the timing of the trigger event, and the timing of the time bin may be set based upon this timing. However, the techniques described herein are not limited in this respect, as any suitable technique may be used to detect the start of a measurement.

Having described the timing of operation of the pixel 100, the discussion now returns to the structure and readout of pixel 100. FIG. 5 shows a cross-sectional view of an example of pixel 100 along the line A-A' in FIG. 2. As illustrated, electrodes 206, 203 and 213 are formed on or over a semiconductor substrate 101. Light is received from a light source 120 at photon absorption/carrier generation area 102. Light source 120 may be any type of light source, including a luminescent sample (e.g., linked to a nucleic acid) or a region or scene to be imaged in imaging applications, by way of example and not limitation. Light source 120 may include unwanted excitation laser light. A light shield 121 may prevent light from reaching another portion of the substrate, for example to prevent charges from being generated directly in the bin or readout node by stray excitation light, or other stray light. Light shield 121 may be formed of any suitable material, such a metal layer of the integrated circuit, by way of example and not limitation. FIG. 5 illustrates the opposite direction of charge transfer during rejection (to the left) and transfer to the bin (right).

Figure 5:
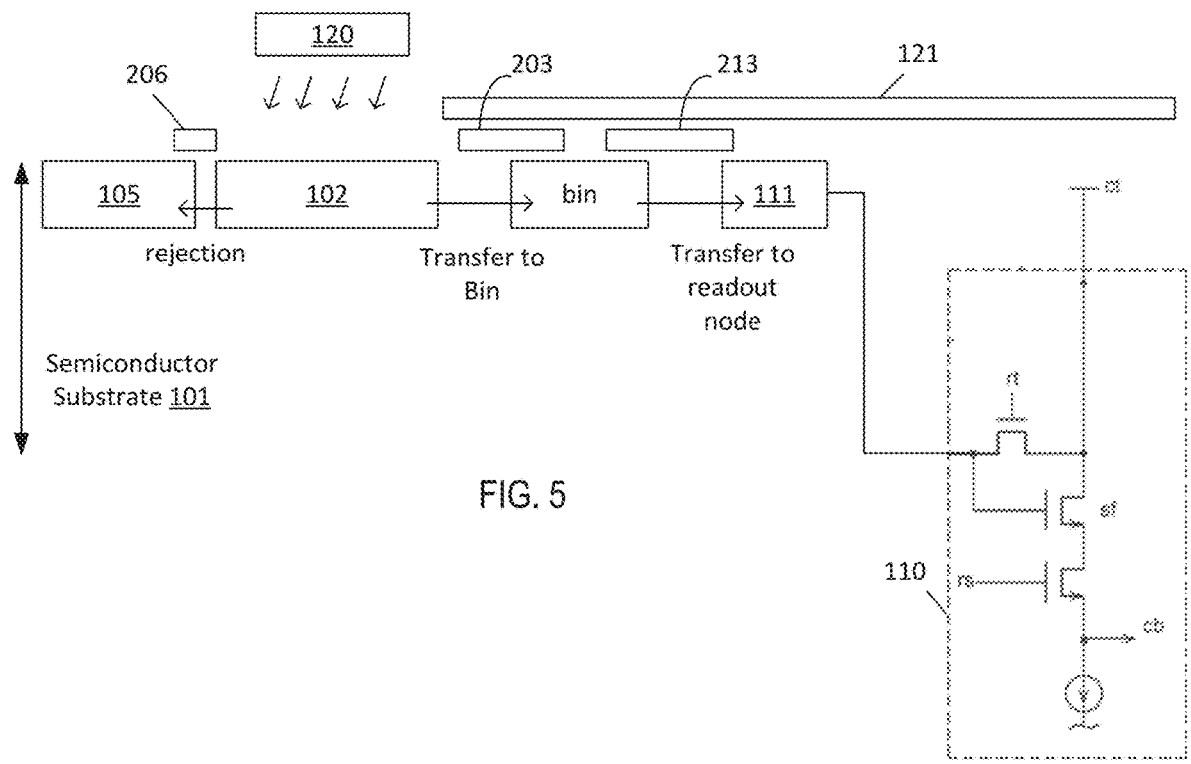
FIG. 5 shows a cross-sectional view of a direct binning pixel.

As illustrated in FIG. 5, pixel 100 may include readout circuitry 110 that allows reading out the charge stored in the bin. Pixel 100 may be an active pixel, such that readout circuitry 110 includes a readout amplifier, or a passive pixel in which readout circuitry 110 does not include a readout amplifier. Any suitable type of active pixel or passive pixel readout circuitry may be used. If readout circuitry 110 includes a readout amplifier, the readout amplifier may take the charge accumulated in a charge storage bin (e.g., bin 0, bin 1) as an input and produce a voltage representative of the charge in the charge storage bin as an output.

If readout circuitry 110 includes a readout amplifier, any suitable type of amplifier may be used. Examples of suitable amplifiers include amplifiers abased on a common source configuration and amplifiers abased on a source-follower configuration. One example of readout circuitry 110 based on a source-follower configuration is illustrated in FIG. 5. As shown in FIG. 5, readout region 110 may include a source follower buffer transistor sf, a reset transistor rt, and a row select transistor rs. However, the techniques described herein are not limited as to any particular amplifier configuration. In some embodiments, transfer electrode 213 may be part of readout circuitry 110.

Any suitable readout techniques may be used, including noise reduction techniques. In some embodiments, readout circuitry 110 may read out the bin using correlated double sampling. Correlated double sampling is technique in which a first sample may be taken of a node at a reset voltage level which includes an undetermined amount of noise, and a second sample may be taken of a signal level at the node including the same undetermined noise. The noise can be subtracted out by subtracting the sampled reset level from the sampled signal level.

Reading out the bin may include converting the amount of charge aggregated in the bin into a corresponding voltage, as discussed above. Readout from the time bin may be performed at any suitable rate, such as 50 Hz to 100 Hz, 10 Hz to 500 Hz, or another rate.

Transfer electrode 213 may be charge coupled to the bin. A readout node 111 may be charge coupled to the transfer electrode 213. As illustrated in FIG. 5, the readout node 111 may be connected to the source of the reset transistor rt. The drains of the reset transistor rt and row select transistor rs may be connected to a high voltage supply. The gates of the reset transistor rt and row select transistor rs may be controlled by a row driver circuit. In some embodiments, the source of the transistor sf may be connected to the drain of the row select transistor rs. The gate of transistor sf may be connected to the readout node 111. In some embodiments, the source of the source follower may be connected to the column line readout.

Figure 6:
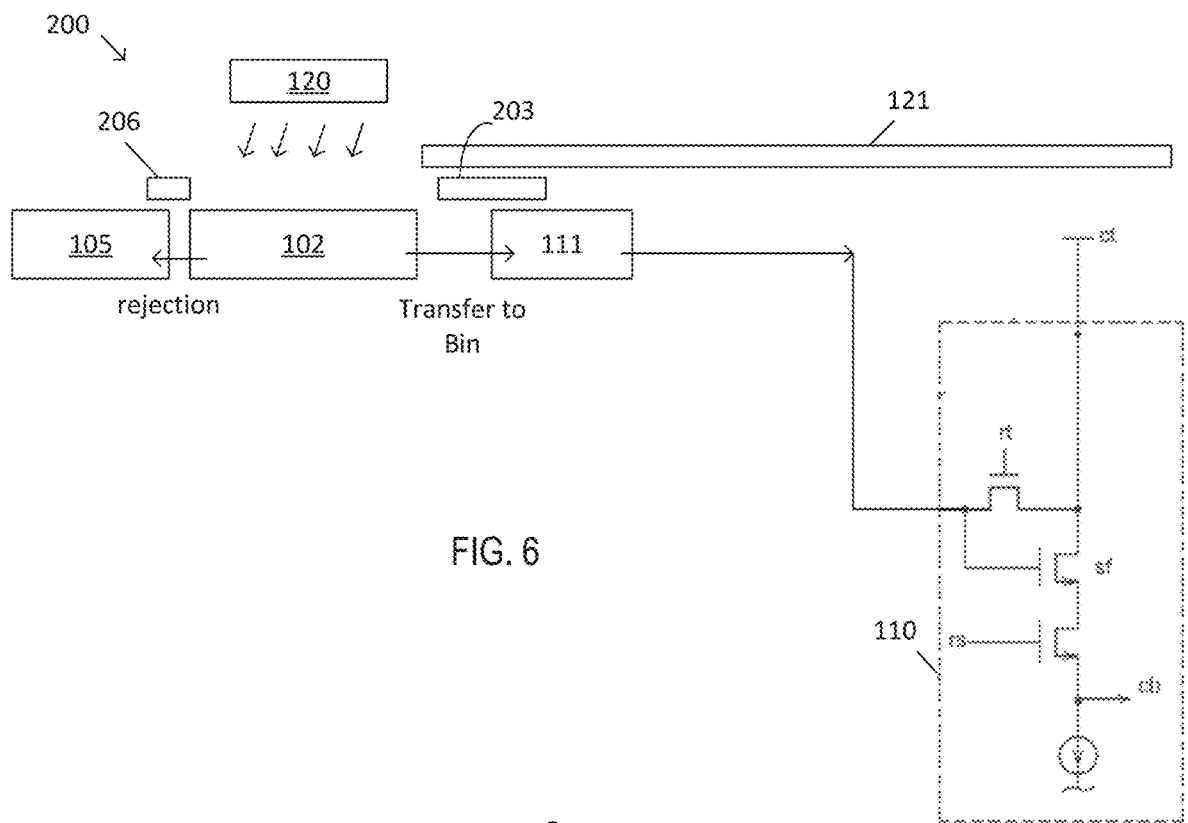
FIG. 6 shows a cross-sectional view of a direct binning pixel in which the bin is formed by a readout node.
Figure 7:
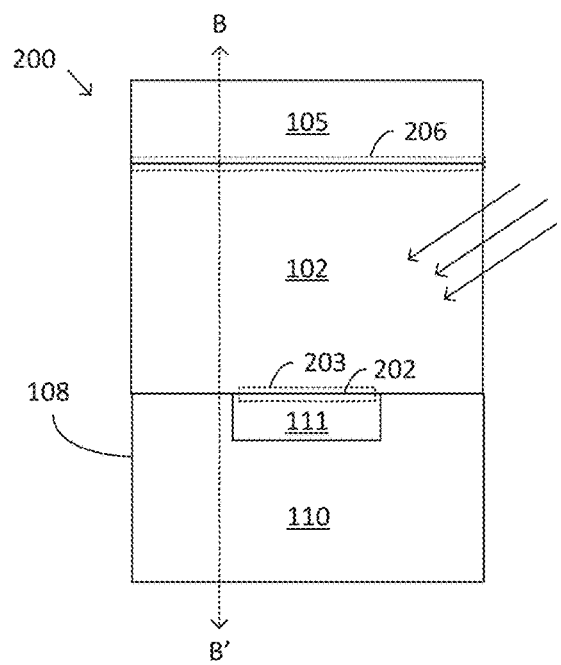
FIG. 7 shows a plan view of the direct binning pixel of FIG. 6.

In some embodiments, a pixel need not have both a bin and a readout node 111. FIG. 6 shows a cross-sectional view of an example of pixel 200, in which the bin is formed by the readout node 111. The readout node 111 may be a floating diffusion, as discussed above. Using readout node 111 as the bin may simplify the pixel design and operation by eliminating a charge storage region and electrode 213. FIG. 7 shows a plan view of pixel 200. As seen in FIGS. 6 and 7, in pixel 200 electrode 203 controls the potential barrier 202 to accessing the readout node 111. Operation of pixel 200 may be the same for that described above for pixel 100, with the exception that readout may be simplified by avoiding the need to transfer charge from a separate bin to readout node 111.

Example Storage Bins

There are several ways to implement a charge storage bin as a potential well within the semiconductor region. In some embodiments, the potential well may be partially within the electrode 203. There are two types of transfer for moving charge in and out of the well. The accumulation transfer moves charge into the well. The readout transfer moves charge out of the well.

The following are possible characteristics of the potential well:
  The well may be of sufficient depth to store accumulated
    charge of at least 100 electrons for 10 ms at 30° C.
  The electrode 203 charge couples region 102 to the well.
  The well may be at least partially within the electrode
    203.
  The well may be at higher potential during accumulation
    transfer than the full depletion voltage of region 102.
  The well's full depletion voltage may be at lower potential than the floating diffusion reset level during readout
    transfer.

The well's potential may be dynamically modulated in order to serve both the requirements of accumulation transfer and readout transfer.

There are a number of techniques to create the potential well for a bin, such as bin 0 or bin 1. As one example, one or more of electrodes 203 and 213 and may be complementary-doped (split-doped). A second option is to place a buried channel n-type implant at the well location that is modulated by the electrode. When the electrode is at high potential the well potential increases beyond the collection region. A third option is to produce a replica diode that is the same as the diode of region 102. The diode may be a buried diode, as with the diode of region 102, that has the same implants. It may be formed between the barrier 202 and the transfer electrode 213. The depletion voltage may be adjusted with n-type implant that extends across the readout transfer gate. The electrode forming barrier 202 may be doped N+ while the readout transfer electrode may be doped P+. In some embodiments, a combination of the above-described techniques may be used to form the potential well for a bin.

The position of a bin may be under an electrode, in a region not covered by the electrode, or both under an electrode and in a region not covered by an electrode. For example, the bin may be under electrode 203, in the region not under electrode 203 between electrode 203 and the polysilicon transfer electrode connected to t1, or both under electrode 203 and in a region not under electrode 203.

Example of Materials

Figure 8:
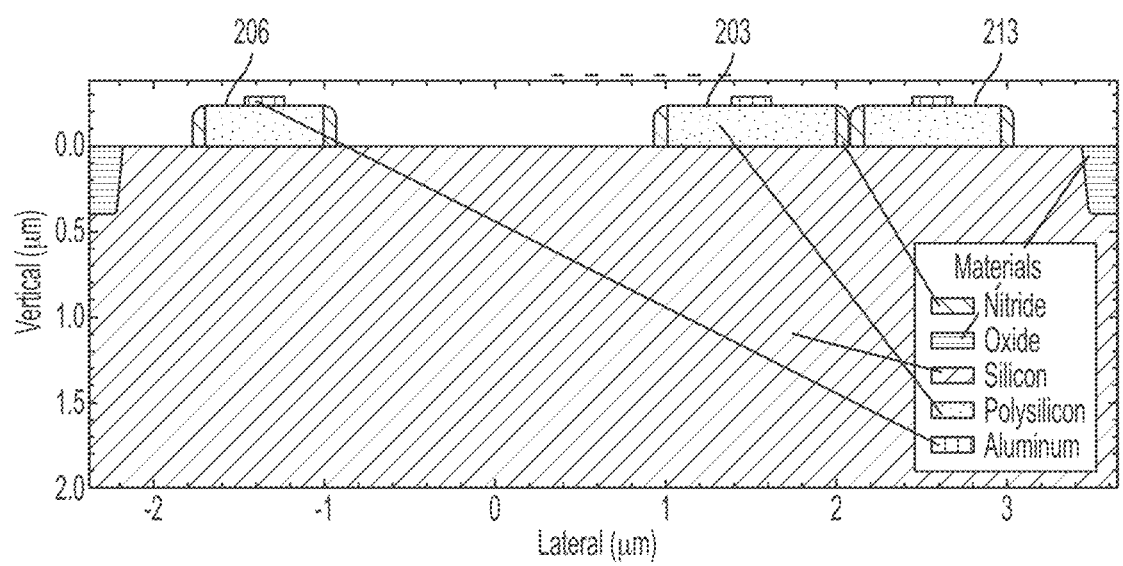
FIG. 8 shows examples of materials from which the integrated circuit may be fabricated.

FIG. 8 shows examples of materials from which the integrated circuit may be fabricated. A pixel may be formed in a semiconductor region, which in some embodiments may be silicon. Insulating regions, such as silicon oxide regions, may insulate areas of the integrated circuit from one another. The electrodes (e.g., electrodes 206, 203 and 213) may be formed of polysilicon or another conductor. Insulating spacers may be positioned at the sides of the electrodes. For example, the insulating regions may be formed of silicon nitride. A metal such as aluminum may be disposed on the electrodes to make electrical contact thereto. However, other materials may be used, as the devices described herein are not limited as to particular materials.

Enhanced Drain

The inventors have recognized and appreciated that a pixel configured to time-bin charge carriers may be sensitive to the capture of stray charge carriers. Stray charge carriers may occur in a pixel due to various processes such as drift, diffusion or photogeneration. Stray charge carriers are undesirable as they may find their way to the photogeneration region and/or time bin(s), ultimately causing noise that obscures the signal desired to be measured i.e., the charge carriers generated in the photodetection region in response to light that is desired to be measured. It would be desirable to capture and discard stray charge carriers.

Drain structures ("drains") are described herein that can improve the ability of a pixel to capture and discard stray charge carriers. Two classes of drains will be described: those that are weakly coupled to the photodetection region; and those that are strongly coupled to the photodetection region. A drain that is weakly coupled to a photodetection region can capture and discard charge carriers that are in a periphery of the pixel outside of the photodetection region. Such a drain may be disposed in the periphery of the pixel.

The periphery of the pixel may include the regions of the pixel outside of the photodetection region and the bin(s), including regions laterally displaced from or below the photodetection region and bin(s). A drain that is weakly coupled to the photodetection region is not coupled to the photodetection region strongly enough to extract charge carriers from the photodetection region when the drain is biased at a typical operating voltage of the pixel. A drain that is strongly coupled to the photodetection region can extract charge carriers from the photodetection region. For example, such a drain may capture and discard charge carriers produced during a period when light is not desired to be measured by the photodetection region by setting the drain to a suitable voltage. A strongly coupled drain may also capture and discard charge carriers outside of the photodetection region from the region surrounding the strongly coupled drain.

Weakly Coupled Drain

Figure 9:
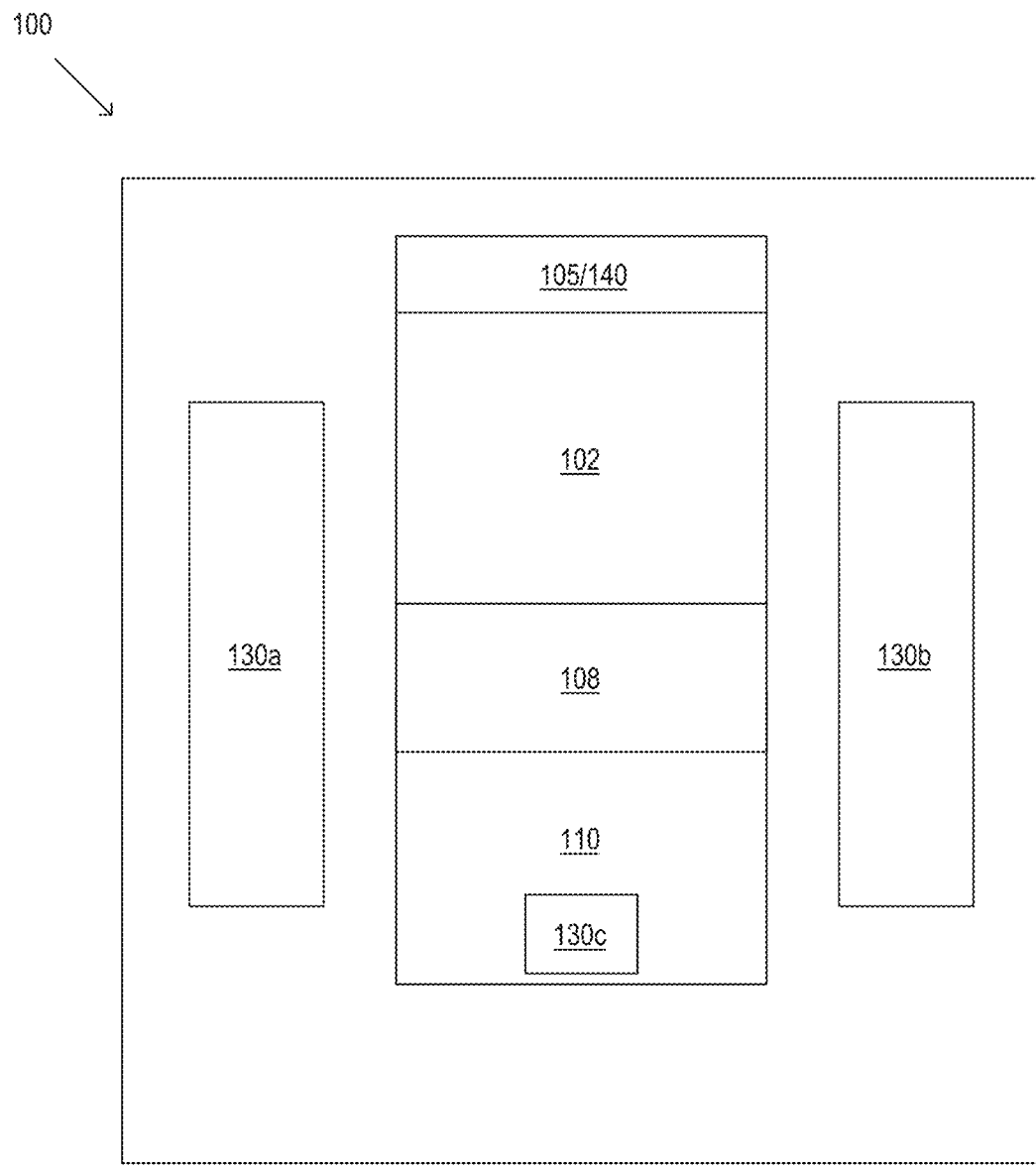
FIG. 9 shows an example of a pixel that can include one or more drains that are weakly coupled to the photodetection region.

FIG. 9 shows an example of a pixel 100 that can include one or more drains 130 that are weakly coupled to the photodetection region 102. Drain(s) 130 may capture and discard stray charge carriers from peripheral region(s) of the pixel 100. To do so, drain(s) 130 may be biased at a suitable electric potential to attract stray charge carriers in the peripheral region(s) of the pixel. As shown in FIG. 9, drain 130a and/or 130b may be separated from the photodetection region 102.

Any number of drains 130 may be included in the pixel 110. The number and position of the drains 130 may be selected based on the locations where stray charge carriers tend to be present. As an example, one or more drains 130a and/or 130b may extend along the sides of the pixel 100, as illustrated in FIG. 9. As another example, a drain 130c may be within the readout region 110 to capture stray charge carriers within the readout region 110 and/or the surrounding regions.

Figure 10A:
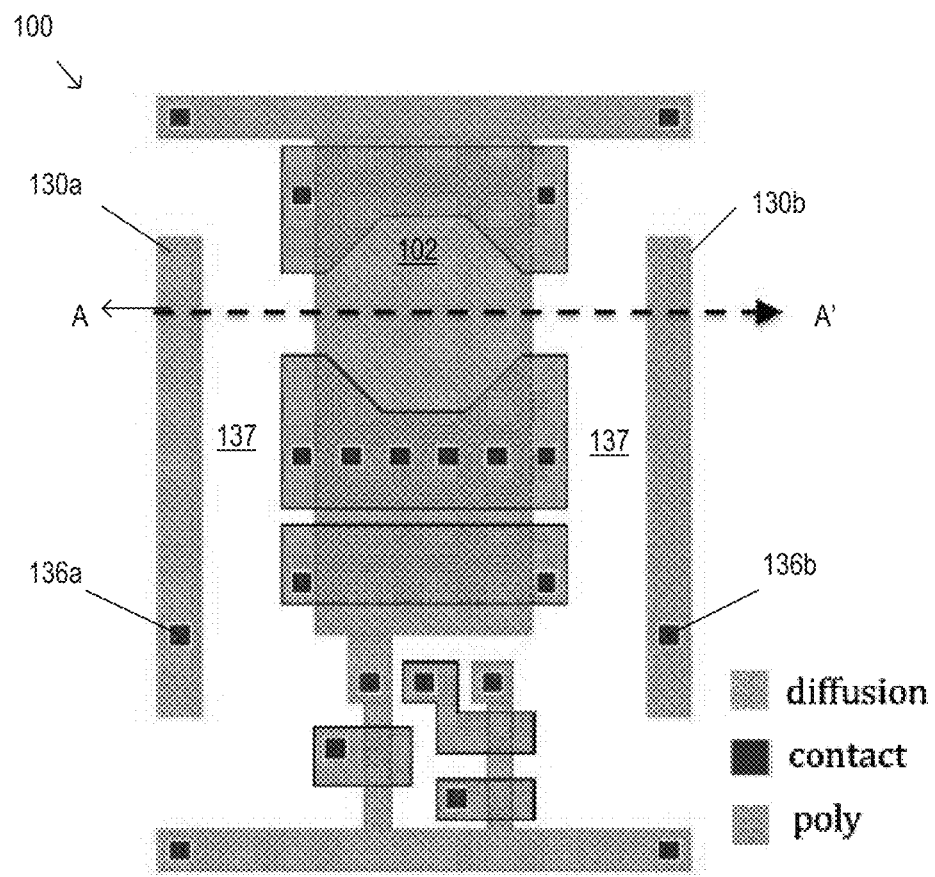
FIG. 10A shows a plan view of a pixel including drains separated from a photodetection region.
Figure 10B:
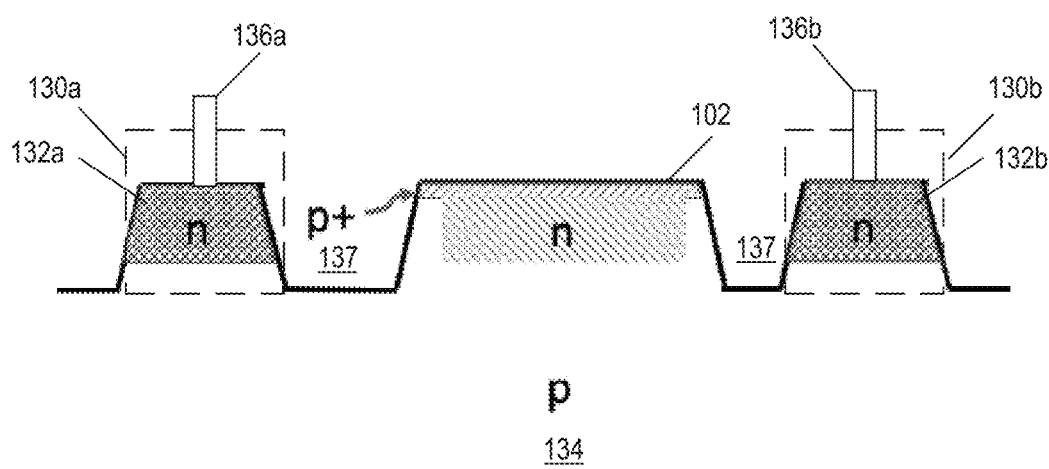
FIG. 10B shows a cross-sectional view of the pixel of FIG. 10A along the line A-A' in FIG. 10A.

FIG. 10A shows a plan view of a pixel 100 including drains 130a and 130b separated from a photodetection region 102. Drains 130a and 130b may be regions of semiconductor. FIG. 10B shows a cross-sectional view of the pixel 100 of FIG. 10A along the line A-A' in FIG. 10A. As illustrated in FIG. 10B, drains 130a, 130b may be raised regions of semiconductor. The drains 130a, 130b may have the same height as photodetection region 102. However, they may have the same or different heights as each other and the photodetection region 102. Trenches 137 of insulating material may be formed between the photodetection region 102 and the drains 130a, 130b. The trenches 137 may be shallow trench insulations (STIs). Drains 130a, 130b may include doped semiconductor regions 132a and 132b, respectively. In this example, the doped semiconductor regions 132a and 132b are doped n-type. Doped semiconductor regions 132a, 132b may be formed using any suitable doping technique, such as implantation or diffusion, for example. Below the doped semiconductor regions is a doped semiconductor region 134 of the opposite doping type. In this example, doped semiconductor region 134 is doped p-type. A p-n junction is formed at the intersection of a region 132 and region 134. The p-n junction may be reverse-biased, and may form a depletion region that sweeps stray carriers into the drain. In some embodiments a Schottky junction may be used instead of or in addition to a p-n junction to establish an electric field that sweeps carriers into the drain.

Contacts 136a and 136b contact the semiconductor regions 132a and 132b, respectively. In some embodiments, contacts 136a, 136b may be metal contacts, such as tungsten plugs, for example. Contacts 136 may directly or indirectly contact the semiconductor region(s) of the drain. In some embodiments, electrical contact may be made to the semiconductor region of the drain through a conductive path that does not include polysilicon. In some embodiments, a silicide or other material may be disposed between the metal contact (e.g., 136) and the single crystal semiconductor material (of region 132). In some embodiments, the silicide may be formed by mixing a refractory metal (e.g., cobalt) with a top region of the single crystal semiconductor. Such a material between the metal and the semiconductor may facilitate establishing an ohmic contact therebetween. In some embodiments, the layer of silicide may be approximately 30 nm thick (e.g., between 15 nm and 45 nm thick). However, the techniques and devices described herein are not limited as to particular thicknesses or particular types of materials.

As illustrated in FIG. 10A, the contacts 136a, 136b may be completely within the area of the corresponding semiconductor region 130 in plan view, such that they not extend beyond the area of the corresponding semiconductor region 130. The contacts 136 may be biased to a voltage such that stray carriers are pulled out through the drain. For example, if the carriers are electrons, the voltage of the contacts 136 may be set to a higher potential than that of the underlying substrate. However, the drains 130 are only weakly coupled to the photodetection region 102 and are not coupled to the photodetection region 102 strongly enough to extract charge carriers from the photodetection region 102 when contacts 136 are biased at an operational voltage of the pixel 100. That is, sufficiently high voltage applied to contacts 136 can cause drains 132 to extract charge carriers from the photodetection region 102, but such a voltage is much higher than the operational voltage range of the pixel 100. Voltages may be applied to various electrodes and devices within the pixel to operate the pixel, and the maximum voltage (in absolute value) relative to ground applied to such electrodes and devices is below the voltage (in absolute value) that would be needed to cause a weakly coupled drain to extract charge carriers from the photodetection region.

Figure 10C:
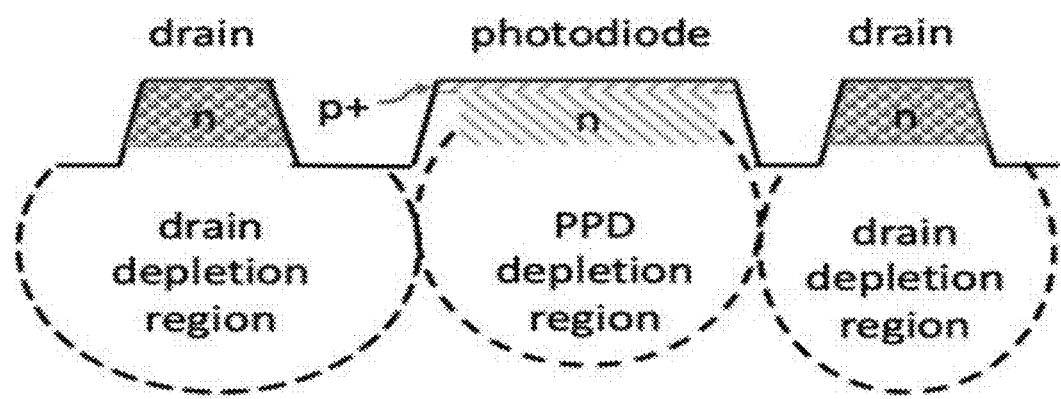
FIG. 10C illustrates that the depletion regions of the drains may form a connected depletion region under the photodiode to pinch off the current path from devices to the substrate.

A combination of properly-placed drains can be used to create a depletion region under the pixel array that helps pinch off the current path from the surface to the substrate. This can be useful to enable "negative substrate bias". Negative substrate bias can substantially improve rejection of stray carriers without loss of quantum efficiency. This concept is shown in FIG. 10C. The depletion regions of the drains may form a connected depletion region under the photodiode to pinch off the current path from devices to the substrate. There are multiple ways of forming a connected depletion region under the pixel array to enable negative substrate bias. One concept described here uses reverse biased junctions. It is also possible to combine this concept with other methods such as adding an n-type implant under the p-wells of the pixel array.

In the example of FIG. 10B, the photodetection region 102 is a pinned photodiode having a highly doped p+ pinned region at the upper surface and an underlying n type doped region. However, the techniques described herein are not limited to photodetection region 102 being a pinned photodiode, as other types of photodetection regions could be implemented, such as photodiodes that are not pinned or photogates, for example.

Figure 11:
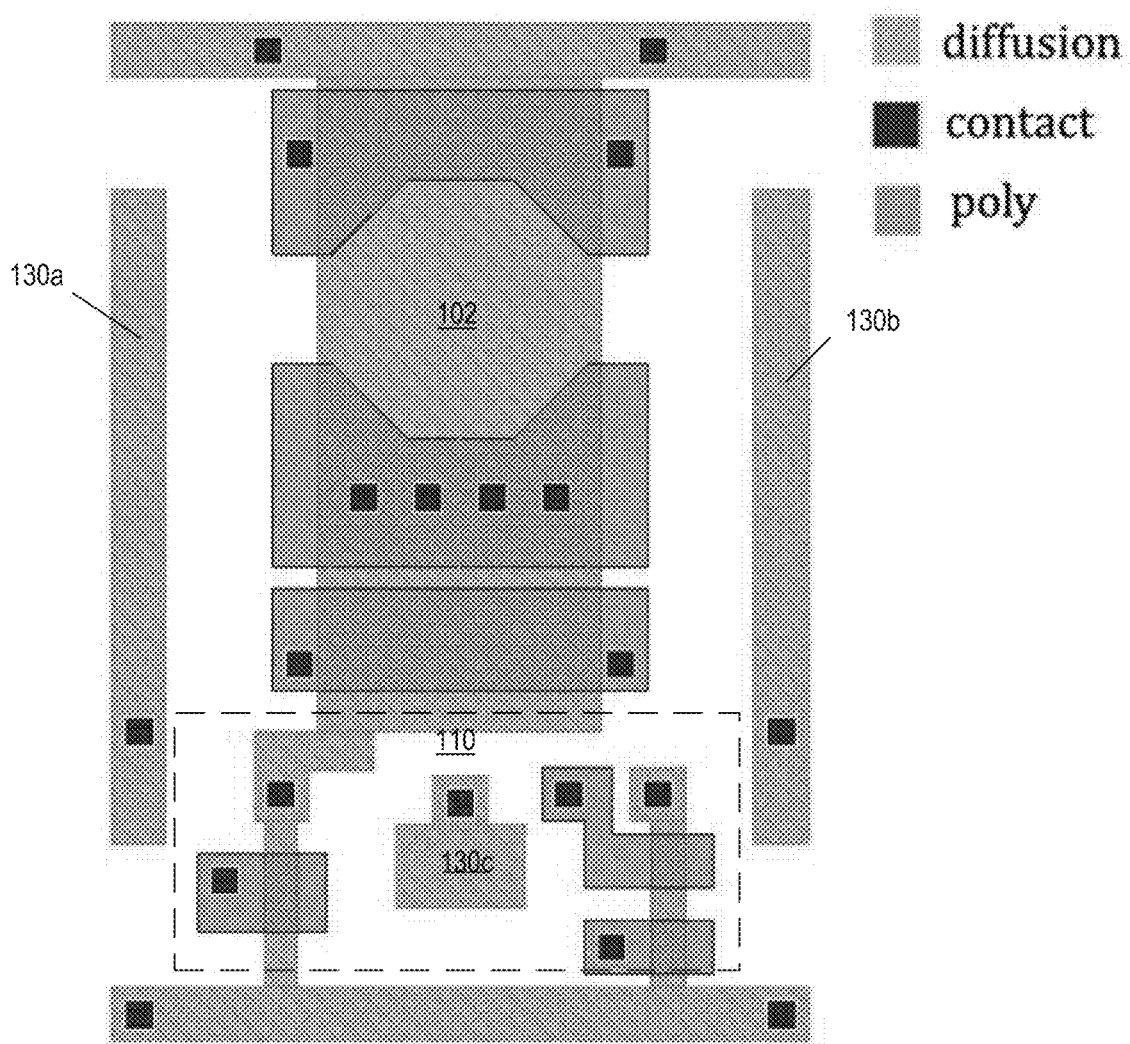
FIG. 11 shows an example of a pixel that includes a drain in the readout region.

FIG. 11 shows an example of a pixel that includes a drain 130c in the readout region 130. Drain 130c may capture stray charge carriers in and under the readout region 110. Drain 130c may be structured and biased in a similar manner as discussed above with respect to drains 130a and 130b. Any number of drains 130c may be provided in the readout region 110, and in any suitable location(s) within readout region 130c. Also illustrated in FIG. 11 are PWELL regions corresponding to p-type doped region 134 in FIG. 10B.

Figure 12:
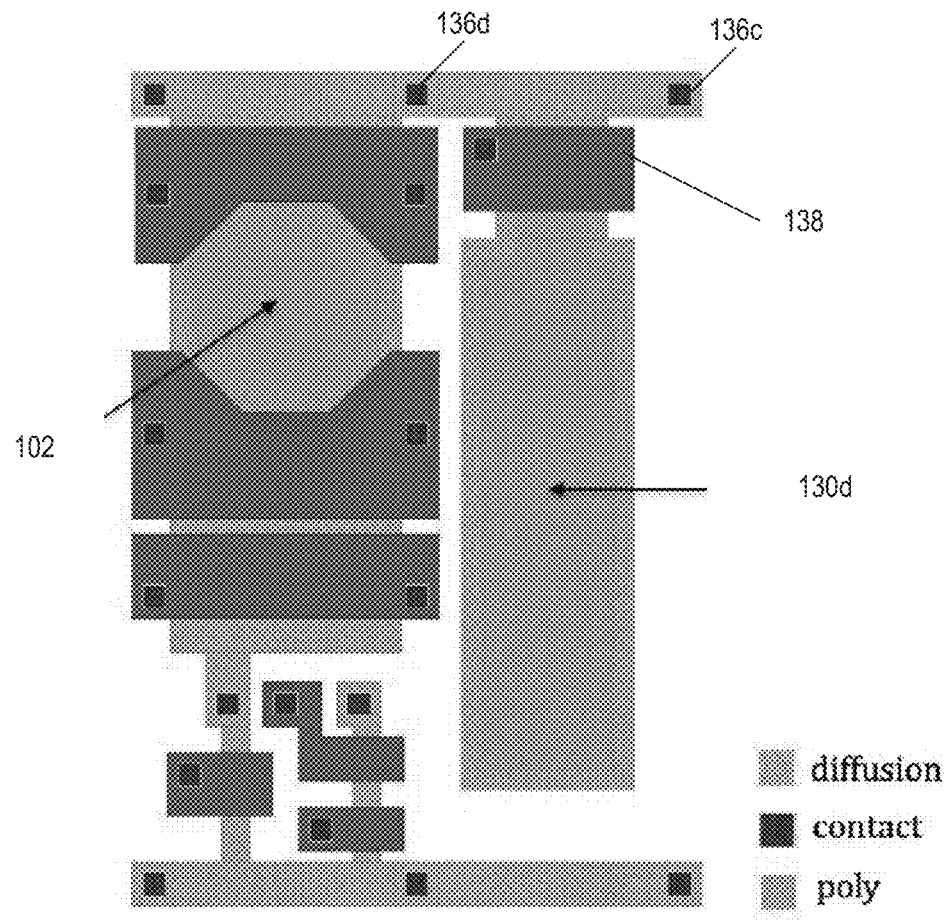
FIG. 12 shows an example of a pixel that includes a drain that is similar in structure and composition to the photodetection region.

FIG. 12 shows an example of a pixel that includes a drain 130d that is similar in structure and composition to the photodetection region 102. For example, the photodetection region 102 may be a pinned photodiode and the drain 130d may also be a pinned photodiode. In some embodiments, the photodetection region 102 and drain 130d may be formed of the same materials, and may have the same doping profiles. However, the techniques described herein are not limited in this respect. Drain 130d may have the function of collecting stray charge carriers, as with other types drains 130. Similarly to photodetection region 102, drain 130d may be partially covered by an electrode 138 separating the photodiode portion of drain 130d from the contacts 136c, 136d. However, such an electrode is optional as long as the drain region is connected to a drain voltage to which the unwanted charge carriers can be discarded.

Strongly Coupled Drain

In some embodiments, a drain may be strongly coupled to the photodetection region. Such a drain may extract unwanted charge carriers from the photodetection region, such as those produced in response to an excitation light pulse. Such a drain may also collect stray charge carriers from regions outside of the photodetection region or bin(s). In some embodiments, a strongly coupled drain includes a semiconductor region that is directly or indirectly contacted by a metal contact without providing the electrical control through a polysilicon electrode and dielectric gate. In cases where the drain needs to be switched on and off, the elimination of the polysilicon electrode can reduce parasitic capacitance on the switching electrode which reduces current draw and power dissipation on the switching electrode.

Figure 13:
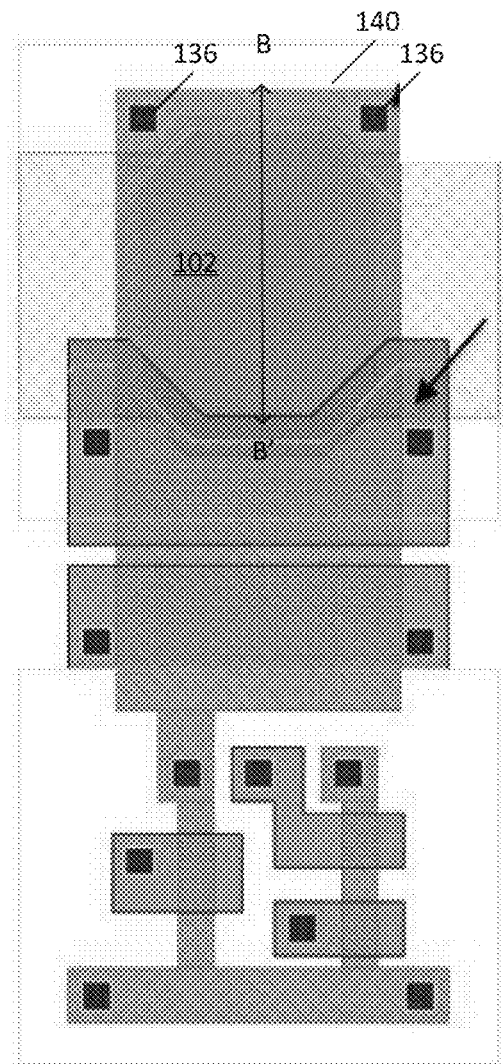
FIG. 13 shows a plan view of a pixel with a drain that is strongly coupled to the photodetection region.

FIG. 13 shows a plan view of a pixel with a drain 140 that is strongly coupled to the photodetection region 102. Drain 140 may include a region of semiconductor proximate the photodetection region 102. One or more contacts 136 may contact the semiconductor region of the drain. Contacts 136 may be metal contacts such as tungsten plugs, for example. In contrast to prior techniques involving a polysilicon electrode, contacts 136 may directly contact the semiconductor region(s) of the drain 140. Said another way, electrical contact may be made to the semiconductor region of the drain through a conductive path that does not include a polysilicon electrode and dielectric gate. In some embodiments, a silicide or other material may be disposed between the metal contact (e.g., 136) and the single crystal semiconductor material (of drain 140). In some embodiments, the silicide may be formed by mixing a refractory metal (e.g., cobalt) with a top region of the single crystal semiconductor. Such a material between the metal and the semiconductor may facilitate establishing an ohmic contact therebetween. In some embodiments, the layer of silicide may be approximately 30 nm thick (e.g., between 15 nm and 45 nm thick). However, the techniques and devices described herein are not limited as to particular thicknesses or particular types of materials.

Figure 14:
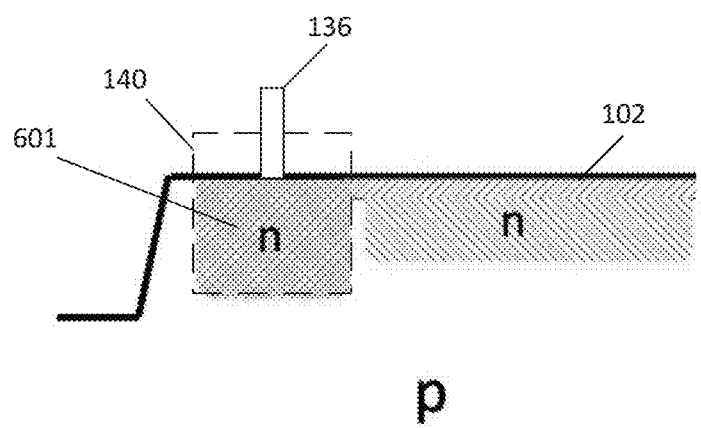
FIG. 14 shows an example of a cross-section along the line B-B' in FIG. 13.

FIG. 14 shows one example of a cross-section along the line B-B' in FIG. 13. In this example, the drain includes a semiconductor region 601 that is doped n-type. The semiconductor region 601 may contact the highly doped p+ layer of the pinned photodiode.

Figure 15A:
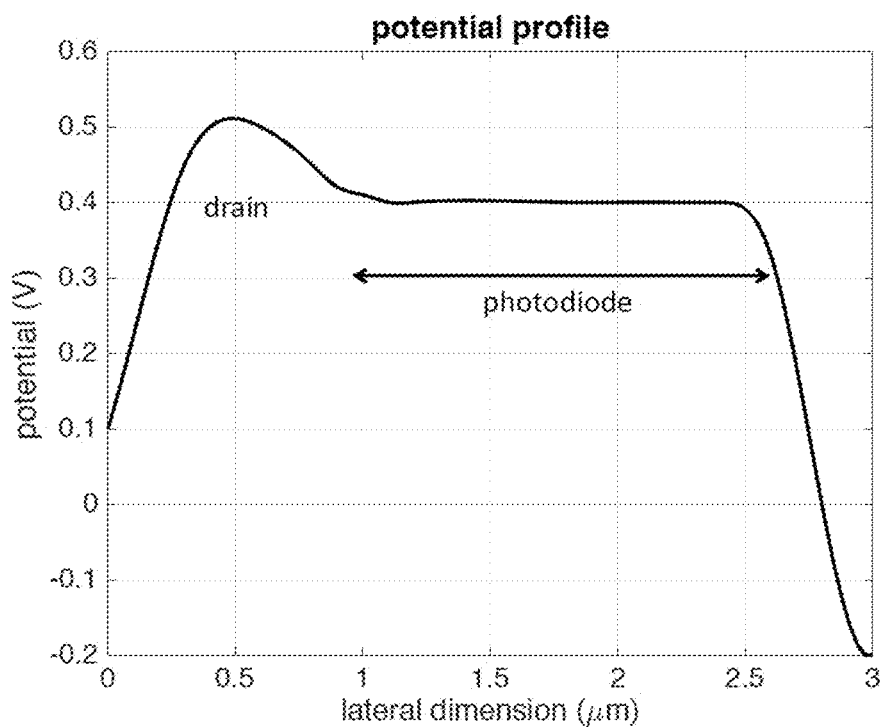
FIGS. 15A and 15B show electric potentials in the photodiode along the line B-B' of FIG. 13 when voltages of 0V and 2V are applied to the drain, respectively.
Figure 15B:
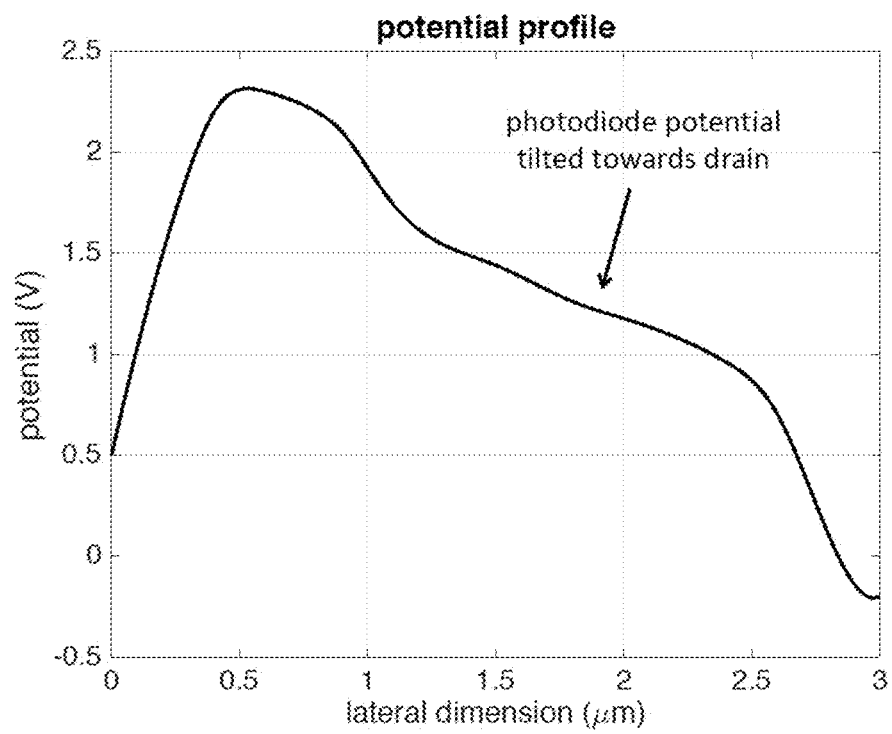

FIGS. 15A and 15B show electric potentials in the photodiode along the line B-B' of FIG. 13 when voltages of 0V and 2V are applied to the drain 140, respectively. As shown in FIG. 15A, applying a voltage of 0V to the drain allows the potential to remain substantially constant across the photodiode, which allows photogenerated carriers to remain in the photodiode for long enough to be collected by a second collection gate, despite limited leakage to the drain. As shown in FIG. 15B, applying a voltage of 2V tilts the electric field in the photodiode and pulls electrons in the photodiode into the drain 140.

Figure 16:
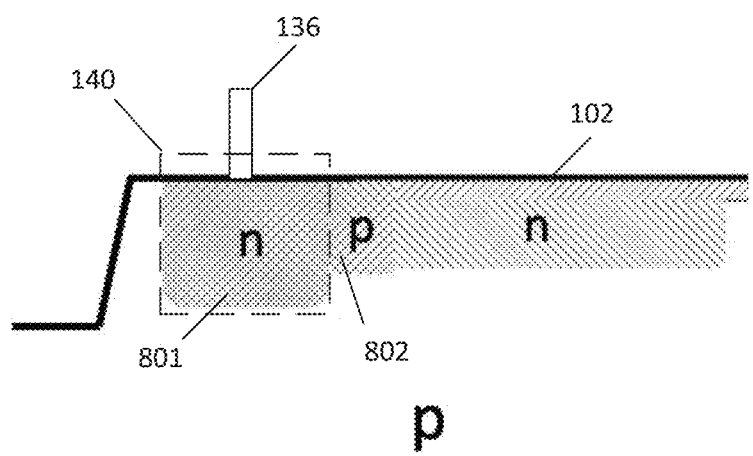
FIG. 16 shows another example of a cross-section along the line B-B' in FIG. 13 of a structure doped to produce a potential barrier between the photodiode and the drain.

FIG. 16 shows another example of a cross-section along the line B-B' in FIG. 13 of a structure doped to produce a potential barrier between the photodiode and the drain. In this example, the drain 140 includes a semiconductor region 801 that is doped n-type separated from the photodiode by a semiconductor region 802 that is doped p-type. Semiconductor region 802 may be a p-type implant using boron or $BF_2$, for example. In contrast to the structure in FIG. 14, there is a potential barrier between the photogeneration region 102 and the drain when the drain is at low voltages. This reduces the competition between this drain and a second collect gate that is intended to capture the carriers generated by a fluorescence dye, for example, leading to a higher collection efficiency of the sensor.

Figure 17A:
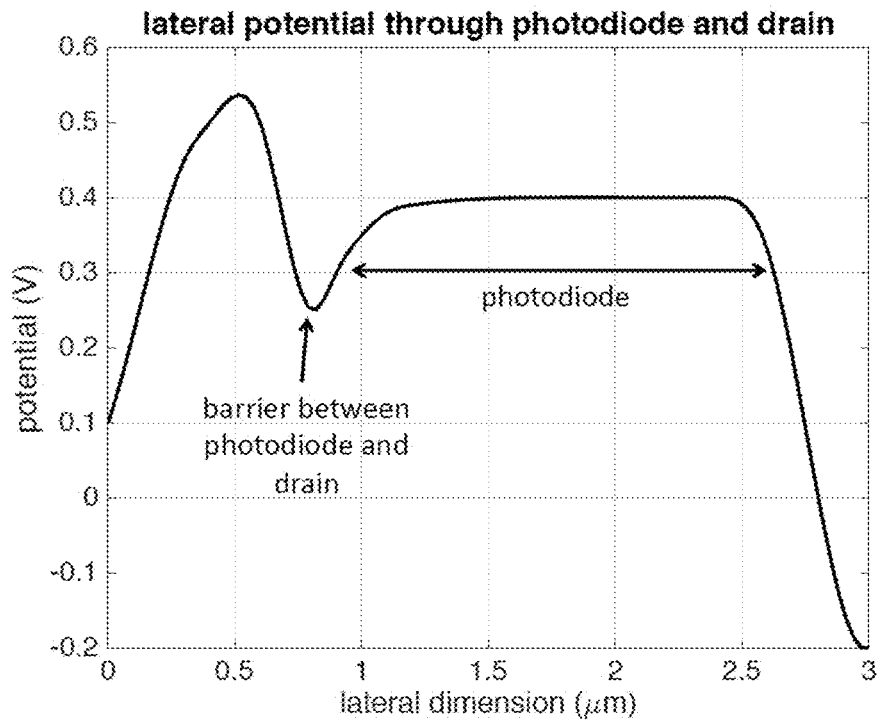
FIGS. 17A and 17B show electric potentials in the photodiode along the line B-B' of FIG. 13 when voltages of 0V and 2V are applied to the drain, respectively.
Figure 17B:
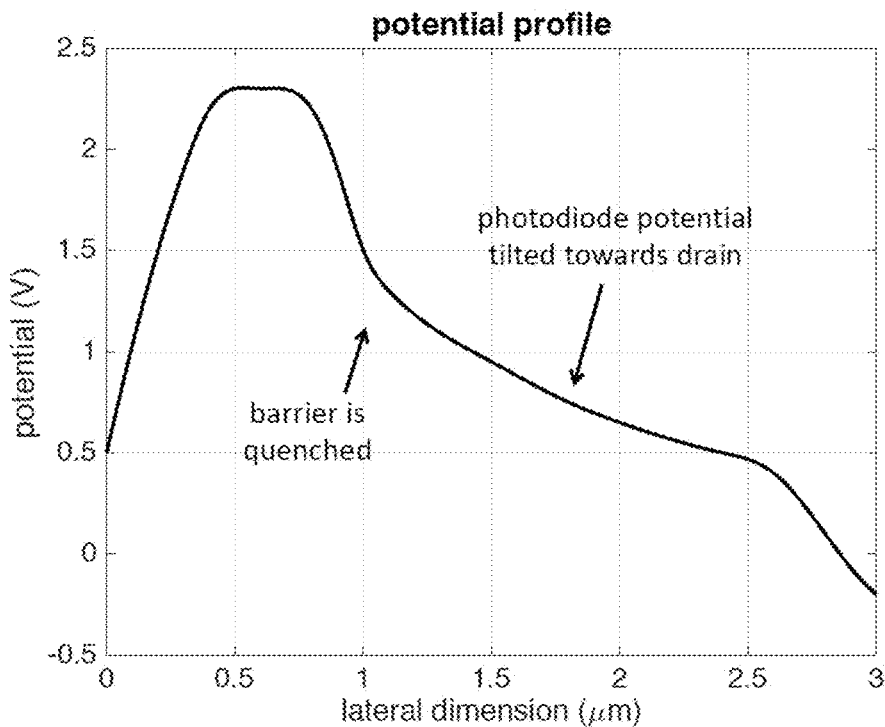

FIGS. 17A and 17B show electric potentials in the photodiode along the line B-B' of FIG. 13 when voltages of 0V and 2V are applied to the drain 140, respectively. As shown in FIG. 17A, when 0V is applied to the drain 140 a potential barrier is formed by the p-n junction between regions 801 and 802. As shown in FIG. 17B, applying a voltage of 2V tilts the electric field in the photodiode and quenches the barrier, allowing electrons in the photodiode to flow into the drain 140.

In a device in which the charge carriers are holes instead of electrons the doping types of the semiconductor regions as well as the biasing voltages may be reversed in polarity, with p-type being replaced by n-type and vice versa, and high voltage being replaced with low voltage and vice versa.

In some embodiments, a pixel may have both one or more weakly coupled drains and one or more strongly coupled drains. For example, returning to discussion of FIG. 9, a pixel may have one or more strongly coupled drains (105 or 140) and one or more weakly coupled drains 130. Providing a pixel with both one or more weakly coupled drains and one or more strongly coupled drains can enhance extraction of unwanted charge carriers.

Pixel Array/Chip Architecture

Figure 18:
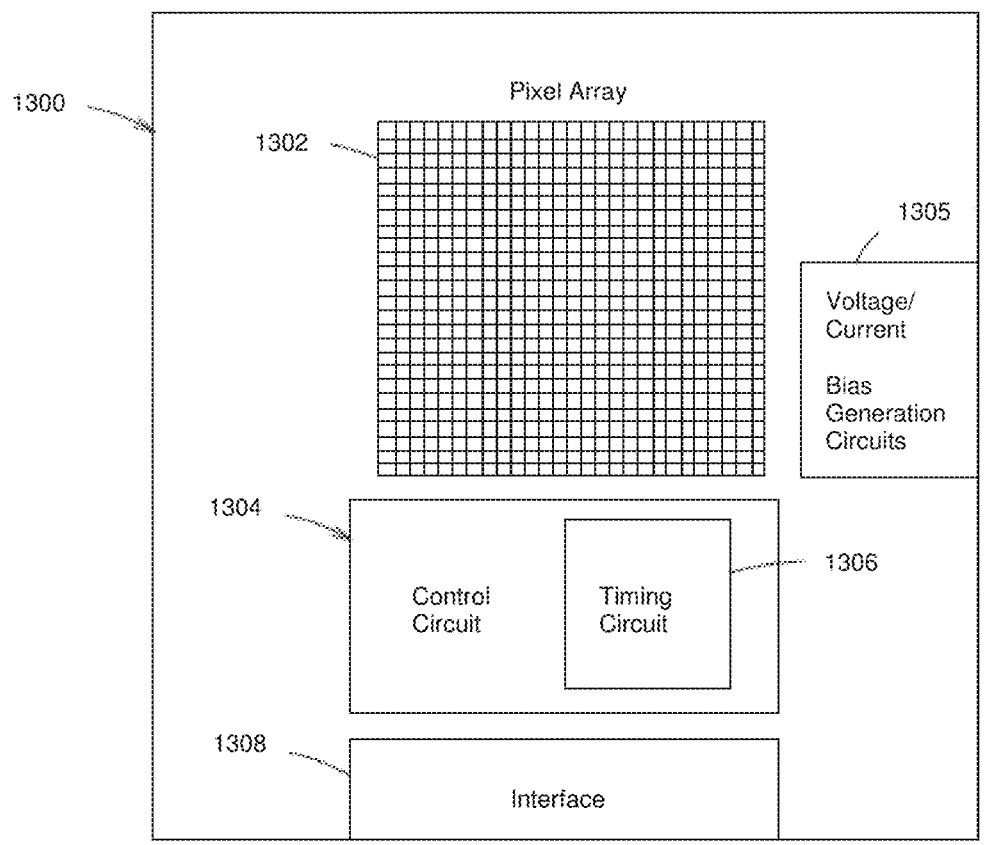
FIG. 18 shows a diagram of the chip architecture, according to some embodiments.

FIG. 18 shows a diagram of the chip architecture, according to some embodiments. In some embodiments, the chip 1300 in FIG. 18 may be formed in a silicon substrate using a standard CMOS (Complementary Metal Oxide Semiconductor) process. However, the techniques described herein are not limited in this respect, as any suitable substrate or fabrication process may be used. As shown in FIG. 18, an integrated circuit or chip 1300 may include a pixel array 1302 including a plurality of pixels 100, a control circuit 1304 that includes a timing circuit 1306, voltage/current bias generation circuits 1305 and an interface 1308. However, not all of these components need be on the chip 1300, as one or more components may be off-chip. For example, in some embodiments control signals for the pixel electrodes may be generated by a circuit located off-chip.

Pixel array 1302 includes an array of pixels 100 laid out in any suitable pattern, such as a rectangular pattern, for example. The pixel array 1302 may have any suitable number of pixels. The pixel array may have row and/or column conductors for reading out rows or columns of the pixel array 1302. Pixels may be read out in parallel, in series, or a combination thereof. For example, in some embodiments a row of pixels may be read out in parallel, and each row of the pixel array may be read out sequentially. However, the techniques described herein are not limited in this respect, as the pixels may be read out in any suitable manner.

The pixel array 1302 is controlled by a control circuit 1304. Control circuit 1304 may be any suitable type of control circuit for controlling operations on the chip 1300, including operations of the pixel array 1302. In some embodiments, control circuit 1304 may include a microprocessor programmed to control operations of the pixel array 1302 and any other operations on the chip 1300. The control circuit may include a computer readable medium (e.g., memory) storing computer readable instructions (e.g., code) for causing the microprocessor performing such operations. For example, the control circuit 1304 may control producing voltages to be applied to electrodes of the charge carrier segregation structure(s) in each pixel. The control circuit 1304 may change the voltages of one or more electrodes, as discussed above, to capture carriers, transfer carriers, and to perform readout of pixels and the array. The control circuit may set the timing of operations of the charge carrier segregation structure based on a stored timing scheme. The stored timing scheme may be fixed, programmable and/or adaptive, as discussed above.

The control circuit 1304 may include a timing circuit 1306 for timing operations of the charge carrier segregation structure(s) of the pixels or other operations of the chip. In some embodiments, timing circuit 1306 may enable producing signals to precisely control the timing of voltage changes in the charge carrier segregation structure(s) to accurately time bin charge carriers. In some embodiments the timing circuit 1306 may include an external reference clock and/or a delay-locked loop (DLL) for precisely setting the timing of the signals provided to the charge carrier segregation structure(s). In some embodiments, two single-ended delay lines may be used, each with half the number of stages aligned 180-degrees out of phase. However, any suitable technique may be used for controlling the timing of signals on the chip.

The chip 1300 may include an interface 1308 for sending signals from the chip 1300, receiving signals at the chip 1300, or both. The interface 1308 may enable reading out the signals sensed by the pixel array 1302. Readout from the chip 1300 may be performed using an analog interface and/or a digital interface. If readout from the chip 1300 is performed using a digital interface, the chip 1300 may have one or more analog to digital converters for converting signals read out from the pixel array 1302 into digital signals. In some embodiments, the readout circuit may include a Programmable Gain Amplifier. One or more control signals may be provided to the chip 1300 from an external source via interface 1308. For example, such control signals may control the type of measurements to be performed, which may include setting the timing of the time bin.

Analysis of signals read out from the pixel array 1302 may be performed by circuitry on-chip or off-chip. For example, in the context of fluorescence lifetime measurement, analysis of the timing of photon arrival may include approximating a fluorescence lifetime of a fluorophore. Any suitable type of analysis may be performed. If analysis of signals read out from the pixel array 1302 is performed on-chip, chip 1300 may have any suitable processing circuitry for performing the analysis. For example, chip 1300 may have a microprocessor for performing analysis that is part of or separate from control circuit 1304. If analysis is performed on-chip, in some embodiments the result of the analysis may be sent to an external device or otherwise provided off-chip through interface 1308. In some embodiments all or a portion of the analysis may be performed off-chip. If analysis is performed off-chip, the signals read out from the pixel array 1302 and/or the result of any analysis performed by the chip 1300, may be provided to an external device through interface 1308.

In some embodiments, the chip 1300 may include one or more of the following:

1) on-chip, digitally controlled, pixel bias generators (DACs).

2) on-chip, digitally programmable gain amplifiers that convert the single-ended pixel output voltage signal to a differential signal and applies gain to the signal 3) digitally-controlled amplifier bias generators that allow scaling the power dissipation with the output rate.

Fabrication Techniques

As mentioned above, a chip having the drains described herein may be formed in a CMOS process. An example of a suitable process is described below. In some embodiments, the same or a similar process may be used as that that described in U.S. Published Patent Application 2018/0180546, filed Dec. 22, 2017, titled "INTEGRATED PHOTODETECTOR WITH DIRECT BINNING PIXEL," which is incorporated by reference in its entirety. Such a process may use appropriate masks to form the drains and other structures disclosed herein. However, this is by way of illustration, as a variety of different processes may be used.

1. Wafer start. The wafer may be formed of any type of semiconductor material, examples of which include silicon, germanium and silicon-germanium. The wafer may be any type of wafer, such as a bulk semiconductor wafer, a wafer with epitaxially grown semiconductor material and/or a silicon-on-insulator (SOI) wafer. The deep doped region 134 (e.g., FIG. 10B) may be present in the wafer at this stage.

2. Deep n-well implant and activation, e.g., using a rapid thermal anneal (RTA) or another type of thermal anneal. This step can be switched with STI loop step 3, depending on node and foundry.

3. STI loop, e.g., to etch silicon to form trenches 137.

4. Well implants and activation, which may include threshold adjust and anti-punch-through implants.

5. Poly gate loop to form gates of the readout transistor(s), for example.

6. Lightly doped drain implants to form the LDD-MOSFET drain, not to be confused with the stray charge collection/rejection drains disclosed herein. Such MOSFETS may be used on the transfer gate and/or readout transistor(s) inside the pixel.

7. Pixel n-type implants, which may be used to form the n-doped region of the photodiode. A single implant or a plurality of implants may be used to form the photodiode. A plurality of implants may help achieve better charge transfer across the photodiode, in some embodiments.

8. Spacer deposition and etch, e.g., to form the spacer on the side(s) of the gate(s) of various transistor(s).

9. S/D (source/drain) implant and activation for the readout transistor(s) for example. The doped regions 132 may be formed in this step, or any other step subsequent to step 8.

10. Pixel p-type implant and activation, which may be used to form the p-doped region of the photodiode.

11. RPO/silicide loop, which may be used to form a silicide between the semiconductor and the metal contacts to form an ohmic contact.

12. Backend (oxide and metal layers on top of silicon). This step may be used to form contacts 136.

Regions 801 and 802 may be formed in any of a number of different steps. For example, they may be formed in step 10 above. As another example, they may be formed in step 9 above, particularly if the region 801 can be formed with the same implant parameters as the source or drain implant. However, regions 801 and 802 may be implants formed with different implant parameters than for the source or drain implants in some cases, which may entail forming them with different masks and/or process loops than for the source or drain implants.

Computing Device

Figure 19:
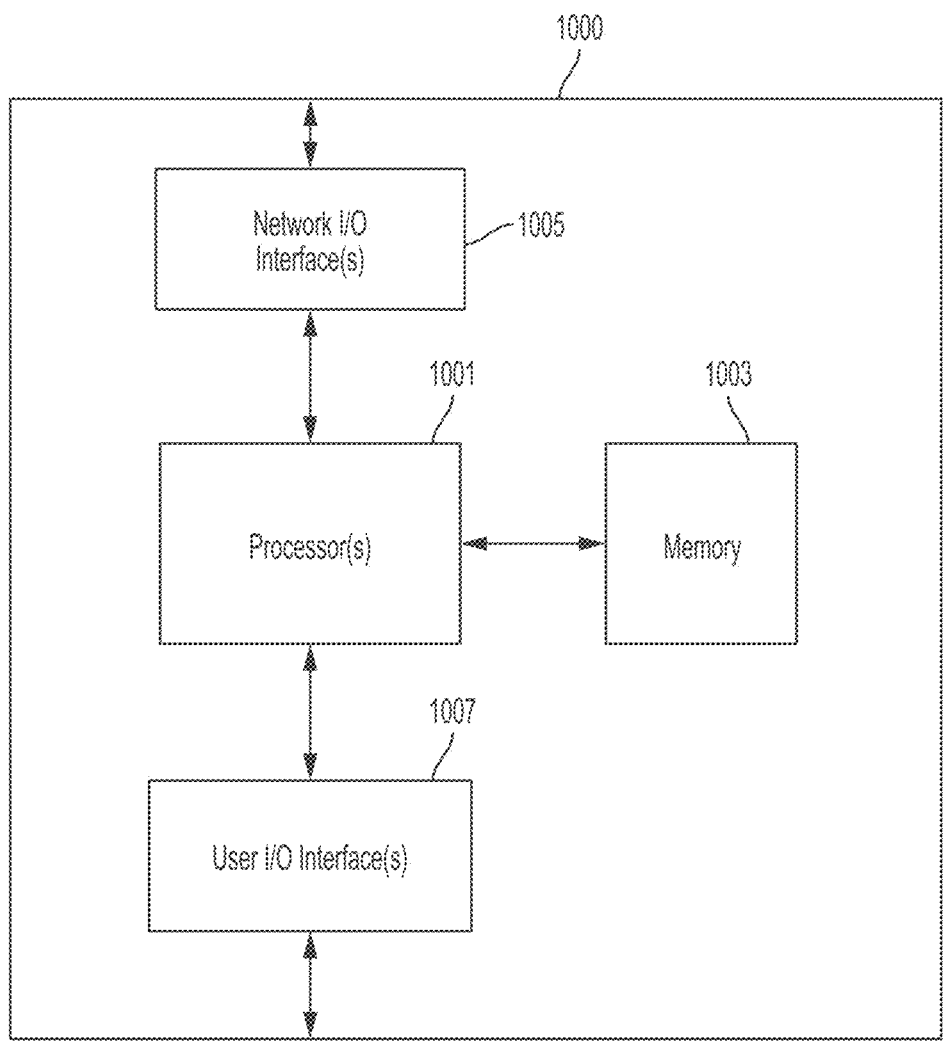
FIG. 19 is a block diagram of an illustrative computing device.

FIG. 19 is a block diagram of an illustrative computing device 1000 that may be used to implement a control circuit for controlling the pixel array or for performing analysis of the data from the pixels. Computing device 1000 may include one or more processors 1001 and one or more tangible, non-transitory computer-readable storage media (e.g., memory 1003). Memory 1003 may store, in a tangible non-transitory computer-recordable medium, computer program instructions that, when executed, implement any of the above-described functionality. Processor(s) 1001 may be coupled to memory 1003 and may execute such computer program instructions to cause the functionality to be realized and performed.

Computing device 1000 may also include a network input/output (I/O) interface 1005 via which the computing device may communicate with other computing devices (e.g., over a network), and may also include one or more user I/O interfaces 1007, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

Additional Applications

Although the integrated photodetector described herein may be applied to the analysis of a plurality of biological and/or chemical samples, as discussed above, the integrated photodetector may be applied to other applications, such as imaging applications, for example. In some embodiments, the integrated photodetector may include a pixel array that performs imaging of a region, object or scene, and may detect temporal characteristics of the light received at individual pixels from different regions of the region, object or scene. For example, in some embodiments the integrated photodetector may perform imaging of tissue based on the temporal characteristics of light received from the tissue, which may enable a physician performing a procedure (e.g., surgery) to identify an abnormal or diseased region of tissue (e.g., cancerous or pre-cancerous). In some embodiments, the integrated photodetector may be incorporated into a medical device, such as a surgical imaging tool. In some embodiments, time-domain information regarding the light emitted by tissue in response to a excitation light pulse may be obtained to image and/or characterize the tissue. For example, imaging and/or characterization of tissue or other objects may be performed using fluorescence lifetime imaging.

Although the integrated photodetector may be applied in a scientific or diagnostic context such as by performing imaging or analysis of biological and/or chemical samples, or imaging tissue, as described above, such an integrated photodetector may be used in any other suitable contexts. For example, in some embodiments, such an integrated photodetector may image a scene using temporal characteristics of the light detected in individual pixels. An example of an application for imaging a scene is range imaging or time-of-flight imaging, in which the amount of time light takes to reach the photodetector is analyzed to determine the distance traveled by the light to the photodetector. Such a technique may be used to perform three-dimensional imaging of a scene. For example, a scene may be illuminated with a light pulse emitted from a known location relative to the integrated photodetector, and the reflected light detected by the photodetector. The amount of time that the light takes to reach the integrated photodetector at respective pixels of the array is measured to determine the distance(s) light traveled from respective portions of the scene to reach respective pixels of the photodetector. In some embodiments, the integrated photodetector may be incorporated into a consumer electronic device such as a camera, cellular telephone, or tablet computer, for example, to enable such devices to capture and process images or video based on the range information obtained.

In some embodiments, the integrated photodetector described in the present application may be used to measure low light intensities. Such a photodetector may be suitable for applications that require photodetectors with a high sensitivity, such as applications that may currently use single photon counting techniques, for example. However, the techniques described herein are not limited in this respect, as the integrated photodetector described in the present applications may measure any suitable light intensities.

Additional Luminescence Lifetime Applications

Imaging and Characterization Using Lifetimes

As mentioned above, the techniques described herein are not limited to labeling, detection and quantitation using exogenous fluorophores. In some embodiments, a region, object or sample may be imaged and/or characterized using fluorescence lifetime imaging techniques though use of an integrated photodetector. In such techniques, the fluorescence characteristics of the region, object or sample itself may be used for imaging and/or characterization. Either exogenous markers or endogenous markers may be detected through lifetime imaging and/or characterization. Exogenous markers attached to a probe may be provided to the region, object, or sample in order to detect the presence and/or location of a particular target component. The exogenous marker may serve as a tag and/or reporter as part of a labeled probe to detect portions of the region, object, or sample that contains a target for the labeled probe. Autofluorescence of endogenous markers may provide a label-free and noninvasive contrast for spatial resolution that can be readily utilized for imaging without requiring the introduction of endogenous markers. For example, autofluorescence signals from biological tissue may depend on and be indicative of the biochemical and structural composition of the tissue.

Fluorescence lifetime measurements may provide a quantitative measure of the conditions surrounding the fluorophore. The quantitative measure of the conditions may be in addition to detection or contrast. The fluorescence lifetime for a fluorophore may depend on the surrounding environment for the fluorophore, such as pH or temperature, and a change in the value of the fluorescence lifetime may indicate a change in the environment surrounding the fluorophore. As an example, fluorescence lifetime imaging may map changes in local environments of a sample, such as in biological tissue (e.g., a tissue section or surgical resection). Fluorescence lifetime measurements of autofluorescence of endogenous fluorophores may be used to detect physical and metabolic changes in the tissue. As examples, changes in tissue architecture, morphology, oxygenation, pH, vascularity, cell structure and/or cell metabolic state may be detected by measuring autofluorescence from the sample and determining a lifetime from the measured autofluorescence. Such methods may be used in clinical applications, such as screening, image-guided biopsies or surgeries, and/or endoscopy. In some embodiments, an integrated photodetector of the present application may be incorporated into a clinical tool, such as a surgical instrument, for example, to perform fluorescence lifetime imaging. Determining fluorescence lifetimes based on measured autofluorescence provides clinical value as a label-free imaging method that allows a clinician to quickly screen tissue and detect small cancers and/or pre-cancerous lesions that are not apparent to the naked eye. Fluorescence lifetime imaging may be used for detection and delineation of malignant cells or tissue, such as tumors or cancer cells which emit luminescence having a longer fluorescence lifetime than healthy tissue. For example, fluorescence lifetime imaging may be used for detecting cancers on optically accessible tissue, such as gastrointestinal tract, bladder, skin, or tissue surface exposed during surgery.

In some embodiments, fluorescence lifetimes may be used for microscopy techniques to provide contrast between different types or states of samples. Fluorescence lifetime imaging microscopy (FLIM) may be performed by exciting a sample with a light pulse, detecting the fluorescence signal as it decays to determine a lifetime, and mapping the decay time in the resulting image. In such microscopy images, the pixel values in the image may be based on the fluorescence lifetime determined for each pixel in the photodetector collecting the field of view.

Imaging a Scene or Object Using Temporal Information

As discussed above, an integrated photodetector as described in the present application may be used in scientific and clinical contexts in which the timing of light emitted may be used to detect, quantify, and or image a region, object or sample. However, the techniques described herein are not limited to scientific and clinical applications, as the integrated photodetector may be used in any imaging application that may take advantage of temporal information regarding the time of arrival of incident photons. An example of an application is time-of-flight imaging.

Time-of-Flight Applications

In some embodiments, an integrated photodetector may be used in imaging techniques that are based on measuring a time profile of scattered or reflected light, including time-of-flight measurements. In such time-of-flight measurements, a light pulse may be is emitted into a region or sample and scattered light may be detected by the integrated photodetector. The scattered or reflected light may have a distinct time profile that may indicate characteristics of the region or sample. Backscattered light by the sample may be detected and resolved by their time of flight in the sample. Such a time profile may be a temporal point spread function (TPSF). The time profile may be acquired by measuring the integrated intensity over multiple time periods after the light pulse is emitted. Repetitions of light pulses and accumulating the scattered light may be performed at a certain rate to ensure that all the previous TPSF is completely extinguished before generating a subsequent light pulse. Time-resolved diffuse optical imaging methods may include spectroscopic diffuse optical tomography where the light pulse may be infrared light in order to image at a further depth in the sample. Such time-resolved diffuse optical imaging methods may be used to detect tumors in an organism or in part of an organism, such as a person's head.

Additionally or alternatively, time-of-flight measurements may be used to measure distance or a distance range based on the speed of light and time between an emitted light pulse and detecting light reflected from an object. Such time-of-flight techniques may be used in a variety of applications including cameras, proximity detection sensors in automobiles, human-machine interfaces, robotics and other applications that may use three-dimensional information collected by such techniques.

Additional Aspects

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. The use of ordinal terms is also not intended to preclude additional elements. For example, recitation of a "first" and "second" element does not preclude presence of a "third" element or additional elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The invention claimed is:

1. A system, comprising:
   an integrated circuit, comprising:
   a pixel, comprising:
   a photodetection region;
   a charge storage region; and
   a drain configured to discard charge carriers from within a semiconductor region of the pixel outside of the photodetection region and outside of the charge storage region, the drain comprising a drain semiconductor region and a conductive contact that contacts the drain semiconductor region;
   wherein the drain is configured to produce a potential barrier between the photodetection region and the drain,
   wherein the system comprises a control circuit configured to operate the pixel to:
   discard, in the drain, charge carriers generated in the semiconductor region in response to excitation light from an excitation light source; and
   collect, in the charge storage region, charge carriers generated in the photodetection region in response to fluorescent emissions excited by the excitation light.

2. The system of claim 1, wherein the drain is configured such that the drain does not extract charge carriers from the photodetection region when the drain is biased at a voltage in an operational voltage range of the pixel.

3. The system of claim 1, wherein the drain is maintained at a fixed voltage.

4. The system of claim 1, wherein a voltage of the drain is variable.

5. The system of claim 1, wherein the conductive contact is a metal plug.

6. The system of claim 1, wherein the conductive contact does not extend outside an area of the drain in plan view.

7. The system of claim 1, wherein the semiconductor region is doped.

8. The system of claim 7, wherein the semiconductor region is n-type doped.

9. The system of claim 8, further comprising a second semiconductor region that is p-type doped under the semiconductor region that is n-type doped.

10. The system of claim 1, wherein the semiconductor region is spaced apart from the photodetection region.

11. The system of claim 1, wherein the drain is a first drain and the pixel further comprises a second drain.

12. The system of claim 11, wherein the first drain is on a first side of the photodetection region and the second drain is on a second side of the photodetection region.

13. The system of claim 11, wherein the pixel further comprises a third drain.

14. The system of claim 13, wherein the third drain is within a readout region of the pixel.

15. The system of claim 13, wherein the third drain is configured to discard carriers from the photodetection region.

16. The system of claim 1, wherein the drain comprises a pn junction or a Schottky junction.

17. The system of claim 1, wherein the drain establishes a depletion region that overlaps with a depletion region of the photodetection region.

18. The system of claim 1, wherein the drain is configured to collect and discard charge carriers under pixel circuitry or one or more doped regions.

19. The system of claim 1, wherein the drain is a first drain and the integrated circuit further comprises a second drain, wherein the second drain is configured to discard carriers from the photodetection region.

20. The system of claim 1, wherein the semiconductor region of the pixel is a peripheral region of the pixel.

21. An integrated circuit, comprising:
a pixel, comprising:
a photodetection region configured to receive incident photons substantially in a first direction;
a charge storage region configured to receive charge carriers from the photodetection region substantially in a second direction orthogonal to the first direction; and
a drain configured to discard charge carriers from within a semiconductor region of the pixel that is offset, substantially in a third direction orthogonal to the first and second directions, from the photodetection region, wherein the drain comprises a drain semiconductor region and the drain semiconductor region is contacted by a conductive metal contact;
wherein the drain is configured to produce a potential barrier between the photodetection region and the drain.

22. The integrated circuit of claim 21, wherein the semiconductor region is in contact with the photodetection region.

23. The integrated circuit of claim 21, wherein the semiconductor region is doped.

24. The integrated circuit of claim 23, wherein the semiconductor region is separated from a photodetection region by a second semiconductor region of opposite doping type from that of the semiconductor region.

25. The integrated circuit of claim 21, wherein the drain is controlled to be at a first voltage when the drain pulls charge carriers out of the photodetection region and is controlled to be at a second voltage when the drain does not pull charge carriers out of the photodetection region.

26. The integrated circuit of claim 21, wherein the conductive metal contact does not extend outside an area of the drain in plan view.

27. The integrated circuit of claim 21, further comprising a silicide material between the conductive metal contact and the drain.

28. The integrated circuit of claim 21, wherein there is no polysilicon in an electrical path between the conductive metal contact and the drain.

29. An integrated circuit, comprising:
a pixel, comprising:
a photodetection region; and
a drain configured to discard charge carriers from within a semiconductor region outside of the photodetection region, wherein the drain comprises a drain semiconductor region contacted by a metal contact, and the drain semiconductor region is not connected to the photodetection region by any path that includes an electrode;
wherein the drain is configured to produce a potential barrier between the photodetection region and the drain.

30. The integrated circuit of claim 29, wherein the semiconductor region is in contact with the photodetection region.

31. The integrated circuit of claim 29, wherein the semiconductor region is doped.

32. The integrated circuit of claim 31, wherein the semiconductor region is separated from a photodetection region by a second semiconductor region of opposite doping type from that of the semiconductor region.

33. The integrated circuit of any one of claim 29, wherein the drain is controlled to be at a first voltage when the drain pulls charge carriers out of the photodetection region and is controlled to be at a second voltage when the drain does not pull charge carriers out of the photodetection region.

34. The integrated circuit of claim 29, wherein the drain is configured to produce a potential barrier between the photodetection region and the drain when the drain does not discard charge carriers from the photodetection region.

35. The integrated circuit of claim 29, wherein the metal contact does not extend outside an area of the drain in plan view.

36. An integrated circuit, comprising:
a pixel, comprising:
a photodetection region comprising a first photodiode;
a charge storage region offset from the first photodiode substantially in a first direction and configured to collect charge carriers generated in the first photodiode; and
a second photodiode offset from the first photodiode substantially in a second direction orthogonal to the first direction and configured to generate and drain unwanted charge carriers, the first and second photodiodes being separated by a potential barrier.

37. The integrated circuit of claim 36, wherein the first and second photodiodes have a same doping profile.

38. The integrated circuit of claim 36, wherein the first and second photodiodes are pinned photodiodes.

39. The integrated circuit of claim 36, wherein the pixel comprises a gate to transfer charge carriers from the photodetection region to the charge storage region.

40. The integrated circuit of claim 36, further comprising:
a second pixel adjacent the pixel along the second direction and comprising a second photodetection region,
wherein the second photodiode is between the photodetection region and the second photodetection region.

41. The integrated circuit of claim 40, wherein the second photodiode is configured to generate and drain unwanted charge carriers from between the photodetection region and the second photodetection region.

42. A method of operating an integrated circuit, the integrated circuit comprising a pixel that comprises a photodetection region, a charge storage region, and a drain, the drain including a drain semiconductor region and a metal contact that contacts the drain semiconductor region, and the method comprising:
using a control circuit to operate the pixel to discard charge carriers from within a semiconductor region of the pixel outside of the photodetection region, the charge carriers being generated om the semiconductor region in response to excitation light from an excitation light source; and
using the control circuit to operate the pixel to collect, in the charge storage region, charge carriers generated in the photodetection region in response to fluorescent emissions excited by the excitation light,
wherein the drain produces a potential barrier between the photodetection region and the drain.

43. A method of manufacturing an integrated circuit, the method comprising:
forming a pixel comprising a photodetection region formed to receive incident photons substantially in a first direction, a charge storage region formed to receive charge carriers from the photodetection region substantially in a second direction orthogonal to the first direction, and a drain formed to discard charge carriers from within a semiconductor region of the pixel that is offset, substantially in a third direction orthogonal to the first and second directions, from the photodetection region; and
forming a metal contact contacting a drain semiconductor region of the drain;
wherein the drain is configured to produce a potential barrier between the photodetection region and the drain.

44. A method of manufacturing an integrated circuit, the method comprising:
forming a pixel comprising a photodetection region and a drain configured to discard charge carriers from within a semiconductor region outside of the photodetection region; and
electrically contacting a drain semiconductor region of the drain with a conductive contact, wherein the drain semiconductor region is formed to not be connected to the photodetection region by any path that includes an electrode;
wherein the drain is configured to produce a potential barrier between the photodetection region and the drain.

45. A method of manufacturing an integrated circuit, the method comprising:
forming a pixel comprising a photodetection region comprising a first photodiode, the pixel further comprising a charge storage region offset from the first photodiode substantially in a first direction and formed to collect charge carriers generated in the first photodiode, and the pixel further comprising a second photodiode offset from the first photodiode substantially in a second direction orthogonal to the first direction and formed to generate and drain unwanted charge carriers, the first and second photodiodes being separated by a potential barrier.

* * * * *